US007803768B2

(12) United States Patent
Kangawa et al.

(10) Patent No.: US 7,803,768 B2
(45) Date of Patent: Sep. 28, 2010

(54) METHOD FOR TREATMENT OF HYPERGLYCEMIA IN A SUBJECT IN NEED THEREOF

(75) Inventors: Kenji Kangawa, Kyoto (JP); Takashi Akamizu, Kyoto (JP); Taiga Irako, Kyoto (JP); Shuichi Koda, Osaka (JP); Naomi Wakabayashi, Gunma (JP)

(73) Assignees: Kyoto University, Kyoto (JP); Daiichi Sankyo Company Limited, Tokyo (JP)

( * ) Notice: Subject to any disclaimer, the term of this patent is extended or adjusted under 35 U.S.C. 154(b) by 224 days.

(21) Appl. No.: 11/884,881

(22) PCT Filed: Feb. 23, 2006

(86) PCT No.: PCT/JP2006/303243

§ 371 (c)(1),
(2), (4) Date: Oct. 18, 2007

(87) PCT Pub. No.: WO2006/090767

PCT Pub. Date: Aug. 31, 2006

(65) Prior Publication Data

US 2009/0143284 A1 Jun. 4, 2009

(30) Foreign Application Priority Data

Feb. 23, 2005 (JP) ............................... 2005-046562
Jan. 11, 2006 (JP) ............................... 2006-003219

(51) Int. Cl.
*A61K 38/00* (2006.01)
(52) U.S. Cl. ........................................ 514/12; 530/300
(58) Field of Classification Search .................. None
See application file for complete search history.

(56) References Cited

FOREIGN PATENT DOCUMENTS

| WO | 01/07475 | | 2/2001 |
|---|---|---|---|
| WO | 01/56592 | | 8/2001 |
| WO | 02/060472 | | 8/2002 |
| WO | WO 03/051389 | * | 6/2003 |
| WO | 2004/004772 | | 1/2004 |

OTHER PUBLICATIONS

Malagon et al., Endocr. 144: 5373-5380, 2003.*
L. Li et al., "Effect on Regeneration of Pancreatic β-Cells in Neonatal Streptozotocin-Treated Rats", Diabetes, vol. 53, pp. 608-615, Mar. 2004.
C. Tourrel et al., "Glucagon-Like Peptide-1 and Exendin-4 Stimulate β-Cell Neogenesis in Streptozotocin-Treated Newborn Rats Resulting in Persistently Improved Glucose Homeostasis at Adult Age", Diabetes, vol. 50, pp. 1562-1570, Jul. 2001.
J. Fernandez-Alvarez et al., "Stable and Functional Regeneration of Pancreatic Beta-Cell Population in nSTZ-Rats Treated with Tungstate", Diabetologia, vol. 47, pp. 470-477, 2004.

N. Asanuma et al., "New Analytical Method for Pancreas and Liver Regeneration: Normalization of Streptozotocin-Induced Hyperglycemia by Retrograde Injection of Insulin Producing Cells", Endocrine Journal, vol. 49, No. 4, pp. 449-457, 2002.
Samukawa et al., "An Analysis of Ghrelin Function as a Factor of Gastrointestinal Proliferation and Renaturation", A study on Cloning a New Gastrointestinal Proliferation and Renaturation Factor, Sokatsu Buntan Kenkyu Hokokusho, pp. 29-33, 2004, in Japanese with English translation of Abstract.
E. Adeghate et al., "Ghrelin Stimulates Insulin Secretion from the Pancreas of Normal and Diabetic Rats", Journal of Neuroendocrinoloby, vol. 14, pp. 555-560, 2002.
L. L. Anderson et al., "Physiology of Ghrelin and Related Peptides", Domestic Animal Endocrinology, vol. 29, pp. 111-144, 2005.
M. Korbonits et al., "Ghrelin- A Hormone with Multiple Functions", Frontiers in Neuroendocrinology, vol. 25, pp. 27-68, 2004.
X. Guan et al., "Distribution of mRNA Encoding the Growth Hormone Secretagogue Receptor in Brain and Peripheral Tissues", Molecular Brain Research, vol. 48, pp. 23-29, 1997.
M. Colombo et al., "Effects of Ghrelin and Other Neuropeptides (CART, MCH, Orexin A and B, and GLP-1) on the Release of Insulin from Isolated Rat Islets", Pancreas, vol. 27, No. 2, pp. 161-166, 2003.
M. Kojima et al., "Ghrelin is a Growth-Hormone-Releasing Acylated Peptide from Stomach", Nature, vol. 402, pp. 656-660, Dec. 1999.
M. Nakazato et al., "A Role for Ghrelin in the Central Regulation of Feeding", Nature, vol. 409, pp. 194-198, Jan. 2001.
A. J. Van Der Lely et al., "Biological, Physiological, Pathophysiological, and Pharmacological Aspects of Ghrelin", Endocrine Reviews, vol. 25, No. 3, pp. 426-457, Jun. 2004.
J. P. Chanoine et al., "Ghrelin Gene Expression is Markedly Higher in Fetal Pancreas Compared with Fetal Stomach: Effect of Maternal Fasting", Endocrinology, vol. 145, No. 8, pp. 3813-3820, Aug. 2004.
M. Volante et al., "Expression of Ghrelin and of the GH Secretagogue Receptor by Pancreatic Islet Cells and Related Endocrine Tumors", The Journal of Clinical Endocrinology & Metabolism, vol. 87, No. 3, pp. 1300-1308, Mar. 2002.
M. K. Reimer et al., "Dose-Dependent Inhibition by Ghrelin of Insulin Secretion in the Mouse", Endocrinology, vol. 144, No. 3, pp. 916-921, Mar. 2003.
E. M. Egido et al., "Inhibitory Effect of Ghrelin on Insulin and Pancreatic Somatostatin Secretion", European Journal of Endocrinology, vol. 146, pp. 241-244, 2002.
H. M. Lee et al., "Ghrelin, A New Gastrointestinal Endocrine Peptide that Stimulates Insulin Secretion: Enteric Distribution, Ontogeny, Influence of Endocrine, and Dietary Manipulations", Endocrinology, vol. 143, No. 1, pp. 185-190, Jan. 2002.
C. L. Prado et al., "Ghrelin Cells Replace Insulin-Producing β Cells in Two Mouse Models of Pancreas Development", PNAS, vol. 101, No. 9, pp. 2924-2929, Mar. 2, 2004.

* cited by examiner

*Primary Examiner*—Robert Landsman
*Assistant Examiner*—Gyan Chandra
(74) *Attorney, Agent, or Firm*—Wenderoth, Lind & Ponack, L.L.P.

(57) ABSTRACT

A pharmaceutical for promoting neogenesis or regeneration of pancreatic β cells which produces and secretes insulin and for promoting insulin production in β cells, comprising ghrelin or a derivative thereof as an effective component.

11 Claims, 10 Drawing Sheets

METHOD FOR TREATMENT OF HYPERGLYCEMIA IN A SUBJECT IN NEED THEREOF

This application is a U.S. national stage of International Application No. PCT/JP2006/303243 filed Feb. 23, 2006.

TECHNICAL FIELD

The present invention relates to a pharmaceutical for promoting neogenesis or regeneration of pancreatic β cells producing insulin. The present invention also relates to a method for suppressing or treating hyperglycemia by promoting neogenesis or regeneration of pancreatic β cells.

BACKGROUND TECHNIQUE

Diabetes, also referred to as hyperglycemia, is a metabolic abnormality mainly relating to glucose metabolism, which is caused by, for example, insufficient secretion of insulin or decreased insulin sensitivity of the target cells, and is characterized by high blood sugar. When high blood sugar is sustained for a long period, serious complications in various organs and nerves such as retinopathy, nephropathy and neuropathy may occur mostly due to angiopathy. Therefore, it is currently very important in treatment of diabetes to control and keep blood sugar with the normal range, and means for controlling a blood sugar levels has been conventionally studied.

A glucose tolerance test (an oral load of 75 g glucose) is used for diagnosis of diabetes (hyperglycemia). For this diagnosis, blood is drawn during fasting to measure values of insulin and blood sugar in the blood, and blood is drawn again after a certain time period from intake of water having 75 g of glucose dissolved therein to measure values of insulin and blood sugar in the blood. When a value (ΔIRI/ΔBG) of "a difference in values of blood insulin 30 minutes after the load and before the load" (ΔIRI) divided by "a difference in sugar blood values 30 minutes after the load and before the load" (ΔBG) is not more than 0.4, it is determined that there is a high risk of serious exacerbation of hyperglycemia.

Diabetes is mainly classified into type 1 diabetes and type 2 diabetes. Type 1 diabetes is developed with absolute deficit of insulin secretion caused by debility or death of pancreatic β cells which leads to no or very low insulin secretion. This may be caused by virus infection and autoimmune abnormality originating from virus infection. Type 2 diabetes is developed when insulin secretion from pancreatic β cells is decreased (quantitative insufficiency of insulin), or when insulin action in glucose-uptake cells is decreased (insulin resistance) and, as insulin resistance increases, insulin becomes relatively quantitatively insufficient and blood sugar levels starts to increase. In the latter case, insulin secretion from pancreatic β cells becomes excessive to supply relative quantitative insufficiency of insulin, and when the excessive secretion of insulin reaches a maximum level and is maintained for a long time, pancreatic β cells are finally exhausted and insulin secretion from the cells is decreased.

Therefore, it is assumed that a fundamental cause of diabetes (hyperglycemia) is deficit of pancreatic β cells and decrease in production or insufficiency of secretion of insulin in the cells.

Though an insulin formulation, biguanide agents, sulfonylurea agents, thiazolidinedione agents and the like are currently used for improvement of blood sugar levels, hypoglycemic agents currently used are not yet satisfactory in terms of side effects and the like. Furthermore, since these agents are developed for the purpose of decreasing blood sugar levels, the agents can be used for symptomatic treatment to control blood sugar levels, but are not yet satisfactory from a viewpoint of a curative treatment to improve the fundamental cause of diabetes as described above, that is, deficit of pancreatic β cells themselves and decrease in production or insufficiency of secretion of insulin in the cells.

From the viewpoint as described above, development of an agent capable of promoting neogenesis or regeneration of pancreatic β cells, suppressing exhaustion or death of pancreatic β cells, and further, promoting insulin production in pancreatic β cells is eagerly desired for suppression or treatment of hyperglycemia.

Ghrelin, on the other hand, is a hormone discovered from rat stomach in 1999, which is a peptide having quite a unique chemical structure wherein the 3rd N-terminal amino acid is acylated by a fatty acid (Nature, 402, pp. 656-660, 1999). Ghrelin has been shown to have a function of stimulating secretion of growth hormone from pituitary gland, and has also been shown in a recent study to have a function such as stimulating food intake, or accumulating fat to increase body weight and improve cardiac function (Nature, 409, pp. 194-198, 2001; Endocr. Rev., 25, pp. 426-457, 2004; Front Neuroendocrinol., 25, pp. 27-68, 2004), Ghrelin was isolated and purified from rat as an endogenous growth hormone secretagogue (GHS) for a growth hormone secretagogue receptor (GHS-R). Amino acid sequences of ghrelin having similar primary structures are also known in vertebrates other than rat, for example, human, mouse, porcine, chicken, eel, bovine, equine, ovine, frog, trout, and canine.

```
Human:
GSS(n-octanoyl)FLSPEHQRVQQRKESKKPPAKLQPR    (Sequence No. 1)
GSS(n-octanoyl)FLSPEHQRVQRKESKKPPAKLQPR     (Sequence No. 2)

Rat:
GSS(n-octanoyl)FLSPEHQKAQQRKESKKPPAKLQPR    (Sequence No. 3)
GSS(n-octanoyl)FLSPEHQKAQRKESKKPPAKLQPR     (Sequence No. 4)

Mouse:
GSS(n-octanoyl)FLSPEHQKAQQRKESKKPPAKLQPR    (Sequence No. 5)

Porcine:
GSS(n-octanoyl)FLSPEHQKVQQRKESKKPAAKLKPR    (Sequence No. 6)

Bovine:
GSS(n-octanoyl)FLSPEHQKLQRKEAKKPSGRLKPR     (Sequence No. 7)
```

```
                        -continued
Ovine:
GSS(n-octanoyl)FLSPEHQKLQRKEPKKPSGRLKPR     (Sequence No. 8)

Canine:
GSS(n-octanoyl)FLSPEHQKLQQRKESKKPPAKLQPR    (Sequence No. 9)

Eel:
GSS(n-octanoyl)FLSPSQRPQGKDKKPPRV-NH₂       (Sequence No. 10)

Trout:
GSS(n-octanoyl)FLSPSQKPQVRQGKGKPPRV-NH₂     (Sequence No. 11)
GSS(n-octanoyl)FLSPSQKPQGKGKPPRV-NH₂        (Sequence No. 12)

Chicken:
GSS(n-octanoyl)FLSPTYKNIQQQKGTRKPTAR        (Sequence No. 13)
GSS(n-octanoyl)FLSPTYKNIQQQKDTRKPTAR        (Sequence No. 14)
GSS(n-octanoyl)FLSPTYKNIQQQKDTRKPTARLH      (Sequence No. 15)

Bullfrog:
GLT(n-octanoyl)FLSPADMQKIAERQSQNKLRHGNM     (Sequence No. 16)
GLT(n-decanoyl)FLSPADMQKIAERQSQNKLRHGNM     (Sequence No. 16)
GLT(n-octanoyl)FLSPADMQKIAERQSQNKLRHGNMN    (Sequence No. 17)

Tilapia:
GSS(n-octanoyl)FLSPSQKPQNKVKSSRI-NH₂        (Sequence No. 18)

Catfish:
GSS(n-octanoyl)FLSPTQKPQNRGDRKPPRV-NH₂      (Sequence No. 19)
GSS(n-octanoyl)FLSPTQKPQNRGDRKPPRVG         (Sequence No. 20)

Equine:
GSS(n-butanoyl)FLSPEHHKVQHRKESKKPPAKLKPR    (Sequence No. 21)
```

(In a notation above, an amino acid residue is represented by one letter.)

The above-described peptide has a specific structure wherein a serine residue (S) or a threonine residue (T) in the 3rd position has a side chain hydroxyl group acylated by a fatty acid such as octanoic acid or decanoic acid. Except for ghrelin, there is no example of biologically active peptide having such a hydrophobic modified structure isolated from an organism. This peptide is known to have a potent growth hormone releasing activity and participate in regulation of growth hormone secretion (International Publication WO01/07475).

Since ghrelin and a receptor thereof (GHS-R) are also expressed in a pancreas (Endocrinology, 145, pp. 3813-3820, 2004; Brain Res. Mol. Brain Res., 48, pp. 23-29, 1997; J. Clin. Endocrinol. Metab., 87, pp. 1300-1308, 2002), studies have been made relating to glucose metabolism or insulin secretion, which showed that ghrelin regulates insulin and glucose in blood, and functions of ghrelin to increase blood sugar and suppress or promote insulin secretion have been reported (Pancreas, 27, pp. 161-166, 2003; Endocrinology, 144, pp. 916-921, 2003; Eur. J. Endocrinol., 146, pp. 241-244, 2002; Endocrinology, 143, pp. 185-190, 2002; J. Neuroendcrinol., 14, pp. 555-560, 2002). A function of ghrelin for pancreatic β cells to promote neogenesis or regeneration of the cell, however, has not been suggested.

In addition, though International Publication WO2001/56592 (and US Patent Publications 2001/0020012A1 and 2004/0063636A1) suggests use of a GHS-R 1A receptor ligand including ghrelin as a pharmaceutical for treatment of type 2 diabetes, there is no demonstration as to whether ghrelin can be used as a remedy for type 2 diabetes or not, and whether utility as suggested actually exists or not is not known to those skilled in the art. In addition, though International Publication WO2002/60472 describes a function of ghrelin for obesity, utility for treatment of diabetes has not been demonstrated.

As for the relationship between pancreatic β cells and ghrelin, a phenomenon has been recognized wherein increased ghrelin producing cells (ε cells) substitute for pancreatic β cells when differentiation to β cells is suppressed (Proc. Natl. Acad. Sci., 101, pp. 2924-2929, 2004). Though a possibility of the two kinds of cells being derived from an identical precursor cell, and a future possibility of producing pure β cells group from stem cells or the like using ghrelin producing cells to treat diabetes at a cell level have been suggested, these are mere possibilities and have not been substantiated. In addition, this publication does not suggest or teach that ghrelin has a function of promoting neogenesis or regeneration of pancreatic β cells or promotes insulin production in pancreatic β cells.

DISCLOSURE OF THE INVENTION

Problems to be Solved by the Invention

The purpose of the present invention is to provide a method of promoting neogenesis or regeneration of pancreatic β cells producing and secreting insulin, and to provide a pharmaceutical for suppressing or treating hyperglycemia by promoting neogenesis or regeneration of pancreatic β cells producing and secreting insulin in hyperglycemia caused by no or very low insulin secretion due to debility or death of pancreatic β cells, or in hyperglycemia caused by decreased insulin secretion in pancreatic β cells.

Means for Solving the Problems

As a result of an earnest study to solve the above-described problems, the inventors found that ghrelin has a function of significantly promoting neogenesis or regeneration of pancreatic β cells, and that ghrelin has a function of promoting insulin production in pancreatic β cells. The present invention has completed based on findings as above.

More specifically, the present invention relates to:

(1) a pharmaceutical composition for suppression or treatment of hyperglycemia, comprising as an effective component a peptide selected from the group consisting of a peptide or a non-peptide compound having an activity for increasing intracellular calcium ion concentration by binding to growth hormone secretagogue receptor (GHS-R), a peptide having an amino acid sequence described as sequence No. 1 wherein the 3rd amino acid residue from an amino terminus is a modified amino acid residue having a fatty acid introduced to a side chain of the amino acid residue, and a peptide having an amino acid sequence described as sequence No. 1 with deletion, substitution and/or addition of one to several amino acids within an amino acid sequence of 5th to 28th amino acids from an amino terminus, wherein the 3rd amino acid residue from the amino terminus is a modified amino acid residue having a fatty acid introduced to a side chain of the amino acid residue and the peptide has an activity for increasing intracellular calcium ion concentration by binding to GHS-R, or a pharmaceutically acceptable salt thereof;

(2) the pharmaceutical composition according to the above (1), wherein hyperglycemia is caused by no insulin secretion or very low insulin due to debility or death of pancreatic β cells, or caused by decreased insulin secretion in pancreatic β cells;

(3) the pharmaceutical composition according to the above (2), wherein hyperglycemia is caused by no or very low insulin secretion due to debility or death of pancreatic β cells;

(4) the pharmaceutical composition according to the above (2), wherein hyperglycemia is caused by decreased insulin secretion in pancreatic β cells;

(5) the pharmaceutical composition according to the above any one of (1) to (4), wherein hyperglycemia has a ΔIRI/ΔBG value of not more than 0.4;

(6) the pharmaceutical composition according to the above any one of (1) to (5), wherein the peptide has an amino acid sequence described as sequence No. 1 and a serine residue in the 3rd position from an amino terminus is a modified amino acid residue having a fatty acid introduced to a hydroxyl group of a side chain of the residue;

(7) the pharmaceutical composition according to the above (6), wherein the peptide has an amino acid sequence described as sequence No. 1 and a hydroxyl group of a side chain of a serine residue in the 3rd position from an amino terminus is acylated by an n-octanoyl group;

(8) a pharmaceutical composition for promoting neogenesis or regeneration of pancreatic β cells, comprising as an effective component a peptide selected from the group consisting of a peptide or a non-peptide compound having an activity for increasing intracellular calcium ion concentration by binding to GHS-R, a peptide having an amino acid sequence described as sequence No. 1 wherein the 3rd amino acid residue from an amino terminus is a modified amino acid residue having a fatty acid introduced to a side chain of the amino acid residue, and a peptide having an amino acid sequence described as sequence No. 1 with deletion, substitution and/or addition of one to several amino acids within an amino acid sequence of 5th to 28th amino acids from an amino terminus, wherein the 3rd amino acid residue from the amino terminus is a modified amino acid residue having a fatty acid introduced to a side chain of the amino acid residue and the peptide has an activity for increasing intracellular calcium ion concentration by binding to GHS-R, or a pharmaceutically acceptable salt thereof;

(9) the pharmaceutical composition according to the above (8), wherein the peptide has an amino acid sequence described as sequence No. 1 and a serine residue in the 3rd position from an amino terminus is a modified amino acid residue having a fatty acid introduced to a hydroxyl group of a side chain of the residue;

(10) the pharmaceutical composition according to the above (9), wherein the peptide has an amino acid sequence described as sequence No. 1 and a hydroxyl group of a side chain of a serine residue in the 3rd position from an amino terminus is acylated by an n-octanoyl group;

(11) a pharmaceutical composition for promoting insulin production in pancreatic β cells, comprising as an effective component a peptide selected from the group consisting of a peptide or a non-peptide compound having an activity for increasing intracellular calcium ion concentration by binding to GHS-R, a peptide having an amino acid sequence described as sequence No. 1 wherein the 3rd amino acid residue from an amino terminus is a modified amino acid residue having a fatty acid introduced to a side chain of the amino acid residue, and a peptide having an amino acid sequence described as sequence No. 1 with deletion, substitution and/or addition of one to several amino acids within an amino acid sequence of 5th to 28th amino acids from an amino terminus, wherein the 3rd amino acid residue from the amino terminus is a modified amino acid residue having a fatty acid introduced to a side chain of the amino acid residue and the peptide has an activity for increasing intracellular calcium ion concentration by binding to GHS-R, or a pharmaceutically acceptable salt thereof;

(12) the pharmaceutical composition according to the above (11), wherein the peptide has an amino acid sequence described as sequence No. 1 and a serine residue in the 3rd position from an amino terminus is a modified amino acid residue having a fatty acid introduced to a hydroxyl group of a side chain of the residue;

(13) the pharmaceutical composition according to the above (12), wherein the peptide has an amino acid sequence described as sequence No. 1 and a hydroxyl group of a side chain of a serine residue in the 3rd position from an amino terminus is acylated by an n-octanoyl group;

(14) a method for suppressing or treating hyperglycemia, comprising the step of administering to an individual exhibiting hyperglycemia a peptide selected from the group consisting of a peptide or a non-peptide compound having an activity for increasing intracellular calcium ion concentration by binding to GHS-R, a peptide having an amino acid sequence described as sequence No. 1 wherein the 3rd amino acid residue from an amino terminus is a modified amino acid residue having a fatty acid introduced to a side chain of the amino acid residue, and a peptide having an amino acid sequence described as sequence No. 1 with deletion, substitution and/or addition of one to several amino acids within an amino acid sequence of 5th to 28th amino acids from an amino terminus, wherein the 3rd amino acid residue from the amino terminus is a modified amino acid residue having a fatty acid introduced to a side chain of the amino acid residue and the peptide has an activity for increasing intracellular calcium ion concentration by binding to GHS-R, or a pharmaceutically acceptable salt thereof;

(15) the method according to the above (14), wherein hyperglycemia is caused by no insulin secretion or very low insulin due to debility or death of pancreatic β cells, or caused by decreased insulin secretion in pancreatic β cells;

(16) the pharmaceutical composition according to the above (15), wherein hyperglycemia is caused by no or very low insulin secretion due to debility or death of pancreatic β cells;

(17) the method according to the above (15), wherein hyperglycemia is caused by decreased insulin secretion in pancreatic β cells;

(18) the method according to the above any one of (14) to (17), wherein hyperglycemia has a ΔIRI/ΔBG value of not more than 0.4;

(19) the method according to the above any one of (14) to (18), wherein the peptide has an amino acid sequence described as sequence No. 1 and a serine residue in the 3rd position from an amino terminus is a modified amino acid residue having a fatty acid introduced to a hydroxyl group of a side chain of the residue;

(20) the method according to the above (19), wherein the peptide has an amino acid sequence described as sequence No. 1 and a hydroxyl group of a side chain of a serine residue in the 3rd position from an amino terminus is acylated by an n-octanoyl group;

(21) a method for promoting neogenesis or regeneration of pancreatic β cells, comprising the step of administering to an individual a peptide selected from the group consisting of a peptide or a non-peptide compound having an activity for increasing intracellular calcium ion concentration by binding to GHS-R, a peptide having an amino acid sequence described as sequence No. 1 wherein the 3rd amino acid residue from an amino terminus is a modified amino acid residue having a fatty acid introduced to a side chain of the amino acid residue, and a peptide having an amino acid sequence described as sequence No. 1 with deletion, substitution and/or addition of one to several amino acids within an amino acid sequence of 5th to 28th amino acids from an amino terminus, wherein the 3rd amino acid residue from the amino terminus is a modified amino acid residue having a fatty acid introduced to a side chain of the amino acid residue and the peptide has an activity for increasing intracellular calcium ion concentration by binding to GHS-R, or a pharmaceutically acceptable salt thereof;

(22) the method according to the above (21), wherein the peptide has an amino acid sequence described as sequence No. 1 and a serine residue in the 3rd position from an amino terminus is a modified amino acid residue having a fatty acid introduced to a hydroxyl group of a side chain of the residue;

(23) the method according to the above (22), wherein the peptide has an amino acid sequence described as sequence No. 1 and a hydroxyl group of a side chain of a serine residue in the 3rd position from an amino terminus is acylated by an n-octanoyl group.

(24) a method for promoting insulin production in pancreatic β cells, comprising the step of administering to an individual a peptide selected from the group consisting of a peptide or a non-peptide compound having an activity for increasing intracellular calcium ion concentration by binding to GHS-R, a peptide having an amino acid sequence described as sequence No. 1 wherein the 3rd amino acid residue from an amino terminus is a modified amino acid residue having a fatty acid introduced to a side chain of the amino acid residue, and a peptide having an amino acid sequence described as sequence No. 1 with deletion, substitution and/or addition of one to several amino acids within an amino acid sequence of 5th to 28th amino acids from an amino terminus, wherein the 3rd amino acid residue from the amino terminus is a modified amino acid residue having a fatty acid introduced to a side chain of the amino acid residue and the peptide has an activity for increasing intracellular calcium ion concentration by binding to GHS-R, or a pharmaceutically acceptable salt thereof;

(25) the method according to the above (24), wherein the peptide has an amino acid sequence described as sequence No. 1 and a serine residue in the 3rd position from an amino terminus is a modified amino acid residue having a fatty acid introduced to a hydroxyl group of a side chain of the residue;

(26) the method according to (25), wherein the peptide has an amino acid sequence described as sequence No. 1 and a hydroxyl group of a side chain of a serine residue in the 3rd position from an amino terminus is acylated by an n-octanoyl group;

(27) use of a peptide or a non-peptide compound for producing a pharmaceutical composition for suppression or treatment of hyperglycemia, wherein the peptide is selected from the group consisting of a peptide or a non-peptide compound having an activity for increasing intracellular calcium ion concentration by binding to GHS-R, a peptide having an amino acid sequence described as sequence No. 1 wherein the 3rd amino acid residue from an amino terminus is a modified amino acid residue having a fatty acid introduced to a side chain of the amino acid residue, and a peptide having an amino acid sequence described as sequence No. 1 with deletion, substitution and/or addition of one to several amino acids within an amino acid sequence of 5th to 28th amino acids from an amino terminus, wherein the 3rd amino acid residue from the amino terminus is a modified amino acid residue having a fatty acid introduced to a side chain of the amino acid residue and the peptide has an activity for increasing intracellular calcium ion concentration by binding to GHS-R;

(28) the use according to the above (27), wherein hyperglycemia is caused by no or very low insulin secretion due to debility or death of pancreatic β cells, or caused by decreased insulin secretion in pancreatic β cells;

(29) the use according to the above (28), wherein hyperglycemia is caused by no or very low insulin secretion due to debility or death of pancreatic β cells;

(30) the use according to the above (28), wherein hyperglycemia is caused by decreased insulin secretion in pancreatic β cells;

(31) the use according to the above any one of (27) to (30), wherein hyperglycemia has a ΔIRI/ΔBG value of not more than 0.4;

(32) the use according to the above any one of (27) to (31), wherein the peptide has an amino acid sequence described as sequence No. 1 and a serine residue in the 3rd position from an amino terminus is a modified amino acid residue having a fatty acid introduced to a hydroxyl group of a side chain of the residue;

(33) the use according to the above (32), wherein the peptide has an amino acid sequence described as sequence No. 1 and a hydroxyl group of a side chain of a serine residue in the 3rd position from an amino terminus is acylated by an n-octanoyl group;

(34) use of a peptide or a non-peptide compound for producing a pharmaceutical composition for promoting neogenesis or regeneration of pancreatic β cells, wherein the peptide is selected from the group consisting of a peptide or a non-peptide compound having an activity for increasing intracellular calcium ion concentration by binding to GHS-R, a peptide having an amino acid sequence described as sequence No. 1 wherein the 3rd amino acid residue from an amino terminus is a modified amino acid residue having a fatty acid introduced to a side chain of the amino acid residue, and a peptide having an amino acid sequence described as sequence No. 1 with deletion, substitution and/or addition of one to several amino acids within an amino acid sequence of 5th to 28th amino acids from an amino terminus, wherein the 3rd amino acid residue from the amino terminus is a modified amino acid residue having a fatty acid introduced to a side chain of the amino acid residue and the peptide has an activity for increasing intracellular calcium ion concentration by binding to GHS-R;

(35) the use according to the above (34), wherein the peptide has an amino acid sequence described as sequence No. 1 and a serine residue in the 3rd position from an amino terminus is a modified amino acid residue having a fatty acid introduced to a hydroxyl group of a side chain of the residue;

(36) the use according to the above (35), wherein the peptide has an amino acid sequence described as sequence No. 1 and a hydroxyl group of a side chain of a serine residue in the 3rd position from an amino terminus is acylated by an n-octanoyl group;

(37) use of a peptide or a non-peptide compound for producing a pharmaceutical composition for promoting insulin production in pancreatic β cells, wherein the peptide is selected from the group consisting of a peptide or a non-peptide compound having an activity for increasing intracellular calcium ion concentration by binding to GHS-R, a peptide having an amino acid sequence described as sequence No. 1 wherein the 3rd amino acid residue from an amino terminus is a modified amino acid residue having a fatty acid introduced to a side chain of the amino acid residue, and a peptide having an amino acid sequence described as sequence No. 1 with deletion, substitution and/or addition of one to several amino acids within an amino acid sequence of 5th to 28th amino acids from an amino terminus, wherein the 3rd amino acid residue from the amino terminus is a modified amino acid residue having a fatty acid introduced to a side chain of the amino acid residue and the peptide has an activity for increasing intracellular calcium ion concentration by binding to GHS-R;

(38) the use according to the above (37), wherein the peptide has an amino acid sequence described as sequence No. 1 and a serine residue in the 3rd position from an amino terminus is a modified amino acid residue having a fatty acid introduced to a hydroxyl group of a side chain of the residue;

(39) the use according to the above (38), wherein the peptide has an amino acid sequence described as sequence No. 1 and a hydroxyl group of a side chain of a serine residue in the 3rd position from an amino terminus is acylated by an n-octanoyl group.

(40) a method for suppressing debility, death or wearing out of pancreatic β cells, comprising the step of administering to an individual a peptide selected from the group consisting of a peptide or a non-peptide compound having an activity for increasing intracellular calcium ion concentration by binding to GHS-R, a peptide having an amino acid sequence described as sequence No. 1 wherein the 3rd amino acid residue from an amino terminus is a modified amino acid residue having a fatty acid introduced to a side chain of the amino acid residue, and a peptide having an amino acid sequence described as sequence No. 1 with deletion, substitution and/or addition of one to several amino acids within an amino acid sequence of 5th to 28th amino acids from an amino terminus, wherein the 3rd amino acid residue from the amino terminus is a modified amino acid residue having a fatty acid introduced to a side chain of the amino acid residue and the peptide has an activity for increasing intracellular calcium ion concentration by binding to GHS-R, or a pharmaceutically acceptable salt thereof;

(41) the method according to the above (40), wherein the peptide has an amino acid sequence described as sequence No. 1 and a serine residue in the 3rd position from an amino terminus is a modified amino acid residue having a fatty acid introduced to a hydroxyl group of a side chain of the residue;

(42) the method according to the above (41), wherein the peptide has an amino acid sequence described as sequence No. 1 and a hydroxyl group of a side chain of a serine residue in the 3rd position from an amino terminus is acylated by an n-octanoyl group;

(43) a method for allowing neogenesis or regeneration of pancreatic β cells by allowing a peptide to act on pancreatic β cells or precursor cells of pancreatic β cells isolated from an individual, wherein the peptide is selected from the group consisting of a peptide or a non-peptide compound having an activity for increasing intracellular calcium ion concentration by binding to GHS-R, a peptide having an amino acid sequence described as sequence No. 1 wherein the 3rd amino acid residue from an amino terminus is a modified amino acid residue having a fatty acid introduced to a side chain of the amino acid residue, and a peptide having an amino acid sequence described as sequence No. 1 with deletion, substitution and/or addition of one to several amino acids within an amino acid sequence of 5th to 28th amino acids from an amino terminus, wherein the 3rd amino acid residue from the amino terminus is a modified amino acid residue having a fatty acid introduced to a side chain of the amino acid residue and the peptide has an activity for increasing intracellular calcium ion concentration by binding to GHS-R;

(44) the method according to the above (43), wherein the peptide has an amino acid sequence described as sequence No. 1 and a serine residue in the 3rd position from an amino terminus is a modified amino acid residue having a fatty acid introduced to a hydroxyl group of a side chain of the residue; and

(45) the method according to the above (44), wherein the peptide has an amino acid sequence described as sequence No. 1 and a hydroxyl group of a side chain of a serine residue in the 3rd position from an amino terminus is acylated by an n-octanoyl group.

BEST MODES FOR CARRYING OUT THE INVENTION

Figure 1:
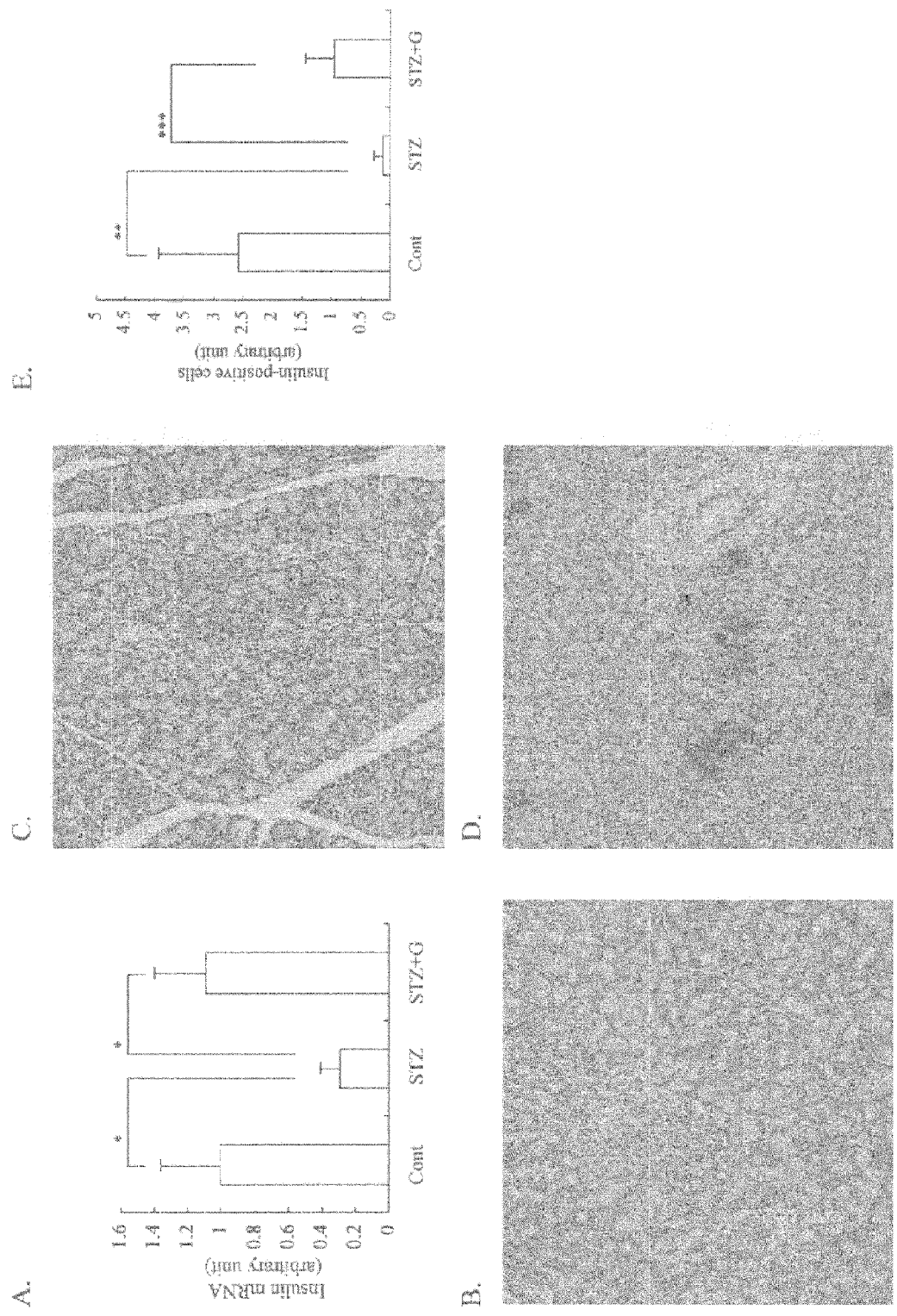
FIG. 1 shows the results for insulin analysis in the pancreas on the 21st day after birth. In this figure, A is a graph indicating insulin gene expression, B-D show results of immunohistological staining of insulin (B shows a control group, C shows an n0-STZ group and D shows an n0-STZ/ghrelin group, respectively with ×100 magnification), and E shows a quantification result for an insulin staining-positive cells area. In each of A and E, "Cont" indicates the control group, "STZ" indicates the n0-STZ group, "STZ+G" indicates the n0-STZ/ghrelin group, and the value for each group is the mean value of three observations±SE. In addition, * indicates P<0.001,  indicates P<0.01, and * indicates P<0.005.

A pharmaceutical of the present invention can be used as a pharmaceutical for an animal (individual) including human. A substance which can be used in the present invention includes a growth hormone secretagogue (GHS), a ligand for growth hormone secretagogue receptor (GHS-R). While known peptide compounds or low molecular-weight compounds can be used as the GHS, a peptide compound ghrelin is especially desirable.

As described above, human-derived ghrelin as well as ghrelin derived from other animals such as rat, mouse, porcine and bovine, and derivatives thereof can be used as ghrelin.

For each individual, ghrelin derived from that individual is desirably used. As an example, human-derived ghrelin is desirably used for a human. Human-derived ghrelin is a peptide consisting of 28 amino acids wherein a hydroxyl group of a side chain of a serine residue in the 3rd position from an amino terminus is acylated by a fatty acid (an n-octanoyl group) (sequence No. 1). An example of a derivative of ghrelin that can be used is a peptide having an amino acid sequence described as sequence No. 1 with substitution, insertion or deletion of one to several amino acids in amino acid residues from 5th to 28th positions from an amino terminus, and having an activity for increasing intracellular calcium ion concentration by binding to growth hormone secretagogue receptor (GHS-R). An amino acid sequence of the derivative desirably has a homology of 70%, preferably 80%, more preferably 90%, especially preferably 95%, and most preferably 97% as compared to a natural form amino acid sequence. This is also applied to ghrelin derived from other animals (sequence Nos. 2-22).

Ghrelin and a derivative thereof used in the pharmaceutical of the present invention can be obtained by ordinary methods. As an example, isolation from a natural raw material or production by a recombinant DNA technique and/or chemical synthesis is possible. When further modification (acylation) of an amino acid residue is required, a modification reaction can be performed according to known means. In a production method using a recombinant DNA technique, for example, it is possible to culture a host cell transformed with an expression vector having DNA coding a peptide according to the present invention, and a target peptide can be collected from the culture to obtain ghrelin or a derivative thereof according to the present invention. Selection of the host cell can result in a compound having the target peptide modified (acylated) in the cell. When the peptide is not modified (acylated), a modification reaction such as acylation may be performed as desired according to known means.

While examples of a vector for introducing a gene thereto include vectors of *Escherichia coli* (pBR322, pUC18, pUC19 and the like), vectors of *Bacillus subtilis* (pUB110, pTP5, pC194 and the like), vectors of yeast (YEp type, YRp type, YIp type), and vectors of animal cells (retrovirus, vaccinia-virus and the like), any other vectors can also be used provided that the vector can stably hold a target gene inside a host cell. The vector is introduced into an appropriate host cell.

Methods described in Molecular Cloninng (Sambrook et al., 1989), for example, can be used as a method of introducing a target gene to a plasmid or a method of introduction into a host cell.

To allow expression of a target peptide gene in the plasmid described above, a promoter can be connected upstream of the gene to function. Any promoter can be used provided that the promoter is suitable for the host cell used to express the target gene. As an example, a lac promoter, a trp promoter, an lpp promoter, a λPL promoter, a recA promoter or the like can be used when the host cell to be transformed is *Escherichia* genus; an SPOL promoter, an $SPO_2$ promoter or the like can be used in a situation of *Bacillus* genus; a GAP promoter, a PHO5 promoter, an ADH promoter or the like can be used in a situation of yeast; and an SV40-derived promoter, a retrovirus-derived promoter or the like can be used in a situation of an animal cell.

A host cell can be transformed using a vector containing a target gene obtained as above. As a host cell, bacteria (for example, *Escherichia* genus or *Bacillus* genus), yeast (*Saccharomyces* genus, *Pichia* genus, *Candida* genus or the like), an animal cell (CHO cells, COS cells or the like) or the like can be used. Liquid medium is suitable as a culture medium, and it is especially preferable that the medium include a carbon source, a nitrogen source and the like required for growth of a transformed cell to be cultured. Vitamins, a growth promoting factor, serum and the like can be added as desired.

For direct production of a fatty acid-modified (acylated) peptide, desirable cells have a processing protease activity capable of cutting a precursor polypeptide of the peptide at an appropriate position, and has an activity allowing acylation of a serine residue in the peptide. Host cells having a processing protease activity and a serine acylation activity as such can be selected by transforming the host cells with an expression vector including cDNA coding the precursor polypeptide, and confirming that transformed cells produce a fatty acid-modified peptide having activity of calcium increase or growth hormone release.

After cultivation, ghrelin can be isolated and purified from the culture by an ordinary method. As an example, to extract a target substance from cultured cell bodies or cells, the cell bodies or cells can be collected after cultivation and suspended in a buffer solution including a protein denaturant (such as guanidine hydrochloride), and then the cell bodies or cells can be homogenized by ultrasonics or the like and subjected to centrifugation thereafter. For purification of the target substance from supernatant, isolation and purification methods such as gel filtration, ultrafiltration, dialysis, SDS-PAGE, and various chromatographies can be appropriately combined and performed considering a molecular weight, solubility, charge (an isoelectric point), affinity and the like of the target substance.

Ghrelin and a derivative thereof can be chemically synthesized by an ordinary method. As an example, ghrelin and a derivative thereof can be obtained by condensing amino acids having protective groups by a liquid-phase method and/or a solid-phase method to extend a peptide chain, removing all of the protective groups with acid, and purifying a resulting crude product with a purification method as described above. A side chain of an amino acid in a target position can be selectively acylated by an acylation enzyme or an acyl transferase.

Various methods of producing peptides are conventionally known, and ghrelin can also be produced readily according to a known method. As an example, ghrelin can be readily produced according to a classical peptide synthesis method or a solid-phase method.

In addition, a production method using a combination of a recombinant DNA technique and chemical synthesis can also be used. Ghrelin can be produced by a method wherein a fragment including a modified amino acid residue is produced by chemical synthesis, while the other fragment not including a modified amino acid residue is produced using a recombinant DNA technique, and thereafter the fragments are fused with each other (see International Publication WO01/07475).

A salt according to ghrelin and a derivative thereof that can be used in the present invention is preferably a pharmaceutically acceptable salt, for example, a salt with an inorganic base, a salt with an organic base, a salt with an inorganic acid, a salt with an organic acid, or a salt with a basic or acidic amino acid.

Suitable examples of a salt with an inorganic base include an alkali metal salt such as sodium salt and potassium salt; an alkaline-earth metal salt such as calcium salt and magnesium salt; and aluminum salt and ammonium salt.

Suitable examples of a salt with an organic base include salts with trimethylamine, triethylamine, pyridine, picoline, ethanolamine, diethanolamine, triethanolamine, dicyclohexylamine, N,N'-dibenzylethylenediamine, and the like.

Suitable examples of a salt with an inorganic acid include salts with hydrochloric acid, hydrobromic acid, nitric acid, sulfuric acid, phosphoric acid, and the like.

Suitable examples of a salt with an organic acid include salts with formic acid, acetic acid, trifluoroacetic acid, fumaric acid, oxalic acid, tartaric acid, maleic acid, citric acid, succinic acid, malic acid, methansulfonic acid, benzenesulfonic acid, p-toluenesulfonic acid, and the like.

Suitable examples of a salt with a basic amino acid include salts with arginine, lysine, ornithine, and the like, and suitable examples of a salt with an acidic amino acid include salts with aspartic acid, glutamic acid, and the like.

Among the salts described above, sodium salt and potassium salt are the most preferred.

Regarding biological actions of ghrelin, a derivative can be selected using binding activity for GHS-R 1A receptor which is a GHS-R, as an indicator, or physiological actions described in the aforementioned publication. A known method can be used as a method of measuring intracellular calcium ion concentration and, for example, FLIPR (Fluorometric Imaging Plate Reader, Molecular Devices) utilizing a change in fluorescence intensity of Fluo-4 AM (Molecular Probe) due to a change in a calcium ion concentration can be used. In addition, a known method can be used to check whether a peptide having a calcium-increasing activity has growth hormone releasing activity in vitro and in vivo. In the case in vitro, for example, the peptide can be added to pituitary gland cells which secrete growth hormone and are shown to express GHS-R, and the growth hormone secreted into the cell culture medium can be measured by radioimmunoassay using an anti-growth hormone antibody. For checking growth hormone releasing activity in vivo, the peptide having a calcium-increasing activity can be injected into a peripheral vein of an animal to measure the serum growth hormone concentration thereafter. In addition, J. Med. Chem., 43, pp. 4370-4376, 2000, for example, can be referred as to a ghrelin derivative and a method for preparation thereof.

As specifically shown in Examples of the present specification, ghrelin and a derivative thereof have a function of promoting neogenesis or regeneration of pancreatic β cells when administered to an individual, and can significantly increase a number of insulin-positive cells in pancreatic β cells. Ghrelin and a derivative thereof also have a function of promoting insulin production in pancreatic β cells and increasing accumulation of insulin in pancreatic β cells.

Though ghrelin has been reported to decrease insulin secretion from pancreatic β cells, a mechanism of production and accumulation of insulin may be different from that of secretion of insulin, and a function of a pharmaceutical of the present invention may be reside in neogenesis or regeneration of pancreatic β cells and promotion of insulin production in pancreatic β cells to increase the amount of insulin storage and thereby increase potential of insulin secretion.

Therefore, by administration of the pharmaceutical of the present invention to an individual, a number of β cells capable of insulin secretion in a pancreas can be increased, and neogenesis or regeneration of pancreatic β cells having insulin secretory function becomes possible.

With this, the pharmaceutical of the present invention having a function of allowing neogenesis or regeneration of pancreatic β cells can be used to suppress debility, death or exhaustion of pancreatic β cells in an individual and protect pancreatic β cells. In addition, development of diabetes can be prevented by administering the pharmaceutical of the present invention to an individual in hyperglycemic condition before diabetes being developed. Furthermore, when condition of diabetes is not serious, progression of morbidity of diabetes can be inhibited by administration of the pharmaceutical of the present invention to an individual. In a situation of serious diabetes (a ΔIRI/ΔBG value of not more than 0.4), a curative treatment of diabetes with neogenesis or regeneration of pancreatic β cells can be performed by administration of the pharmaceutical of the present invention to an individual. Occurrence of neogenesis or regeneration of pancreatic β cells can be demonstrated by, for example, confirming expression of pdx-1, one of principal transcription factors for differentiation of a pancreas.

In addition, regeneration therapy as to pancreatic β cells can be performed by allowing the pharmaceutical of the present invention to act on pancreatic β cells isolated from an individual in a test tube to promote regeneration of pancreatic β cells and proliferation of the cells, and grafting the cells to a site of an individual suffering from debility or death of pancreatic β cells or to a site wherein progression of debility or death of pancreatic β cells is expected. Methods for identification and isolation of precursor cells of pancreatic β cells are currently vigorously studied by many research groups throughout the world, and various methods have been developed (see, for example, Lancet, 364, pp. 203-205, 2004). Neogenesis or regeneration of pancreatic β cells is enabled by allowing ghrelin or a derivative thereof to act on isolated precursor cells of pancreatic β cells, and a cell group obtained as such can be grafted into a living body of an individual to allow regeneration therapy for pancreatic cells.

The pharmaceutical of the present invention, including ghrelin, a derivative thereof or a pharmaceutically acceptable salt thereof as an effective component, can be mixed with a pharmaceutically acceptable carrier, excipient, extender or the like and used for an individual (for example, human, mouse, rat, rabbit, canine, feline, bovine, equine, porcine, ape, etc.). A dose is not specifically limited and can be selected as appropriate corresponding to, for example, an object of use of the pharmaceutical of the present invention, or age, a body weight or a species of the individual. For a human adult, for example, a dose of 50-200 μg as a weight of ghrelin or a derivative thereof can be administered about once or twice a day, or the dose can be administered continuously for about a few days or few weeks.

Ghrelin, a derivative thereof or a pharmaceutically acceptable salt thereof can be mixed with a pharmaceutically acceptable carrier and administered orally or parenterally as a solid preparation such as a tablet, a capsule, granule or powder, or as a liquid preparation such as syrup or an injection.

A variety of organic or inorganic carrier substances commonly used as a preparation material is used as the pharmaceutically acceptable carrier which is mixed as, for example, an excipient, a lubricant, a binder, or a disintegrant in a solid preparation, or as a solvent, a dissolution adjuvant, a suspending agent, an isotonic agent, a buffer, or a soothing agent in a liquid preparation.

In addition, a preparation additive such as a preservative, an antioxidant, a coloring agent, or a sweetener can also be used as required.

Suitable examples of an excipient include lactose, saccharose, D-mannitol, starch, crystalline cellulose, light silicic acid anhydride, and the like. Suitable examples of a lubricant include magnesium stearate, calcium stearate, talc, colloidal silica, and the like.

Suitable examples of a binder include crystalline cellulose, saccharose, D-mannitol, dextrin, hydroxypropylcellulose, hydroxypropylmethylcellulose, polyvinyl pyrrolidone, and the like.

Suitable examples of a disintegrant include starch, carboxymethyl cellulose, calcium carboxymethyl cellulose, croscarmellose sodium, sodium carboxymethyl starch, and the like.

Suitable examples of a solvent include water for injection, an alcohol, propylene glycol, macrogol, sesame oil, corn oil, and the like.

Suitable examples of a dissolution adjuvant include polyethylene glycol, propylene glycol, D-mannitol, benzyl benzoate, ethanol, trisaminomethane, cholesterol, triethanolamine, sodium carbonate, sodium citrate, and the like.

Suitable examples of a suspending agent include surfactants such as stearyltriethanolamine, sodium lauryl sulfate, laurylaminopropionate, lecithin, benzalkonium chloride, benzethonium chloride, and glycerol monostearate; and hydrophilic polymers such as polyvinyl alcohol, polyvinyl pyrrolidone, sodium carboxymethyl cellulose, methylcellulose, hydroxymethylcellulose, hydroxyethylcellulose, and hydroxypropylcellulose.

Suitable examples of an isotonic agent include sodium chloride, glycerol, D-mannitol, and the like.

Suitable examples of a buffer include buffer solutions of phosphate, acetate, carbonate, citrate, and the like.

A suitable example of a soothing agent includes such as benzyl alcohol.

Suitable examples of a preservative include paraoxybenzoates, chlorobutanol, benzyl alcohol, phenethyl alcohol, dehydroacetic acid, sorbic acid, and the like.

Suitable examples of an antioxidant include sulfite, ascorbic acid, and the like.

Examples of a preparation form suitable for parenteral administration include injections for intravenous administration, intradermal administration, hypodermic administration, intramuscular administration and the like, a drip, a suppository, a transdermal absorption agent, a transmucosal absorption agent, and an inhalant, while examples of a preparation form suitable for oral administration include a capsule, a tablet, syrup, and the like. As a preparation form of the pharmaceutical of the present invention, however, the preparation form suitable for parenteral administration, such as an injection, a drip or an inhalant is preferable. Various preparation forms as such are known to those skilled in the art, and those skilled in the art can select a preparation form suitable for a desired administration route as appropriate to produce a preparation in a form of a pharmaceutical composition using, when required, one or more additive for preparation available in the art.

As an example, a pharmaceutical in a form of an injection or a drip can be prepared by dissolving ghrelin or a derivative thereof as an effective component, together with one or more additive for preparation such as an isotonic agent, a pH adjusting agent, a soothing agent, or a preservative, in distilled water for injection and then sterilizing. In addition, a pharmaceutical in a form of an injection or a drip can also be provided as a pharmaceutical in a freeze-dried form. A pharmaceutical as such can be dissolved immediately before use by addition of distilled water for injection, physiological saline or the like, and can then be used as an injection or a drip. In addition, for transmucosal administration, for example, an intranasal administration agent such as a collunarium or an intranasal spray, or an oral cavity administration agent such as a sublingual agent is also suitable.

EXAMPLES

Though the present invention will be described more specifically with examples, the scope of the present invention is not limited to the following examples.

Example 1

1. Material and Method

Female or male Sprague Dawley rats, purchased from Charles River were, were allowed free access to tap water and a standard pellet rat diet (352 kcal/100 g, CE-2, CLEA). Females were caged with a male for one night, and pregnancy was detected by abdominal palpation 14 days later. Natural birth occurred 22 days after mating. We examined three experimental groups as follows: a control group (Sprague Dawley rats) wherein newborn rats received a single intraperitoneal injection of citrate buffer; an n0-STZ group wherein rats received a single intraperitoneal injection of streptozotocin (STZ); and an n0-STZ/ghrelin group wherein rats received a single intraperitoneal injection of streptozotocin, and then received rat-derived ghrelin (hereafter reffered to as rat ghrelin, sequence No. 3, 100 µg/kg body weight) by subcutaneous injection twice a day on the $2^{nd}$ to 8th day after birth for 7 days.

Streptozotocin (Sigma, 100 mg/kg body weight) was dissolved in citrate buffer (0.05 mmol/L, pH4.5) and immediately injected intraperitoneally once into a rat immediately after birth. Pups were left with their mothers. Each neonatal rat was checked for urinary sugar on the 2nd day with Multistix SG (Bayer Medical). Only rats that were glycosuric (3+ value with Multistix SG test) at day 2 after birth were included in the n0-STZ model group. Animals were killed at 21 or 70 days by bleeding under anesthesia with intraperitoneal injection of pentobarbital sodium (50 mg/kg). Blood samples were collected from inferior vena cava, centrifuged immediately at 4° C., and kept at −80° C. until assayed.

After excision, pancreases were removed and weighed. To measure insulin content, pancreases (35-50 mg) were homogenized and centrifuged in 5 ml of acid-ethanol (0.15 M HCl 75% (v/v)-ethanol solution), and the supernatants were kept at −80° C. For immunohistochemistry, additional pancreases were fixed in 4% paraformaldehyde fixative for 24 hours, and embedded in paraffin.

Insulin and pdx-1 were detected immunohistochemically on 3 µm-thick tissue sections using an indirect peroxidase-labeling technique. Each section was incubated with a primary antibody (guinea pig anti-porcine insulin, DACO) or (rabbit anti-mouse/rat IDX-1; CHEMICON) for 1 hour. Staining was performed by incubation with 3,3'-diaminobenzidine tetrahydrochloride (DAB) kit (DakoCytomation). Quantitative evaluations of total β cells area were performed by a computer-assisted image analysis procedure using an Olympus BX 51 microscope connected to a digital camera DP 12 and Mac SCOPE Ver2.6 software (Mitani, Fukui, Japan). β cells area and total pancreatic section area were evaluated for each stained section. A relative volume of β cells was determined by a sterological morphological method, with calculation of the ratio between the areas occupied by immunoreactive cells and those occupied by total pancreatic cells.

Total RNA was extracted from rat pancreases as previously reported (Biochem. Biophys. Res. Commun., 214, pp. 239-246, 1995). To synthesis the first-strand cDNA, the extracted products were used as templates in reactions containing RT (Invitrogen) and the target 3' primer. An RT-PCR analysis was performed according to a method previously reported (Biochem. Biophys. Res. Commun., 214, pp. 239-246, 1995). The first strand cDNA was used in subsequent PCR analyses. In the PCR analyses, oligonucleotide primers as follows were used for each target cDNA. The identity of the PCR product was confirmed by agarose gel electrophoresis.

```
Insulin-1:
5'-tagaccatcagcaagcaggtc      (Sequence No. 22)
3'-cacaccaggtacagagcct        (Sequence No. 23)

Insulin-2:
5'-cacttggtggaagctctctacc     (Sequence No. 24)
3'-gacagggtagtggtgggcctagt    (Sequence No. 25)

Rdx-1:
5'-aggaggtgcatacgcagcag       (Sequence No. 26)
3'-gaggccgggagatgtatttgtt     (Sequence No. 27)
```

Realtime PCR was performed as follows. The cDNA (1 µl) was mixed with 2×PCR Master Mix (Applied Biosystems) (25 µl), sterilized distilled water (23 µl), and sense and anti-sense primers (10 µmol/µl, 0.5 µl) of insulin and Pdx-1. Forty cycles of PCR amplification were carried out using the thermal cycler system (ABI PRISM 7700, Applied Biosystems, Japan), for 15 seconds at 95° C. followed by 60 seconds at 60° C. The concentration of each mRNA product was quantified using calibration curves expressing the fluorescence intensity against the amount of standardized PCR product.

All expression data were normalized to the amount of 18S ribosomal RNA from the same individual sample.

Plasma and blood glucose levels were measured with a glucose analyzer (Antisense 2, Sankyo). Insulin was extracted from pancreases as described (Endocrinology, 140, pp. 4861-4873, 1999). Insulin concentrations were measured with a Lebis insulin ELISA kit (Shibayagi).

Measured values were expressed as means±SEM. Differences between rats of control group STZ-administered group were evaluated by ANOVA, an analysis of variance.

2. Result

The characteristics of the 21-day-old rats are summarized in Table 1. Body weights, fasting blood glucose (FBG) concentrations and insulin concentrations were not significantly different between the control group and the n0-STZ group. The n0-STZ group and the n0-STZ/ghrelin group were also not significantly different from each other regarding these parameters. The FBG concentrations in the n0-STZ/ghrelin group, however, were significantly lower than those of control group ($P<0.01$).

TABLE 1

|  | Control | n0-STZ | n0-STZ/ghrelin |
|---|---|---|---|
| Body Weight (g) | 37.8 ± 5.0 (20) | 37.6 ± 4.8 (15) | 36.3 ± 3.9 (9) |
| FBG (mg/dl) | 114 ± 8.6 (17) | 106.7 ± 16.6 (15) | 100.6 ± 7.6 (8)*[1] |
| Plasma Insulin (ng/ml) | 0.32 ± 0.10 (7) | 0.32 ± 0.19 (6) | 0.35 ± 0.17 (6) |

Each value is the mean ± SE (the number of rats)
*[1]$P < 0.01$ (compared to the control)

Insulin mRNA expression levels within the pancreases were markedly reduced in the n0-STZ group as compared to the control group. These levels, however, returned to levels similar to those of the control group following rat ghrelin treatment (the n0-STZ/ghrelin group) (FIG. 1A). The pancreatic insulin mRNA expression level of the n0-STZ group was about ⅓ of those of the n0-STZ/ghrelin group, but the n0-STZ group exhibited plasma insulin levels comparable to those of the control group and the n0-STZ/ghrelin group. Insulin immunostaining of pancreases was in agreement with the results of gene expression (FIGS. 1A-E). An islet of Langerhans was smaller in the n0-STZ group as compared to the control group (FIGS. 1B, C, E). An islet of Langerhans in the n0-STZ/ghrelin group was larger than that of the n0-STZ group but smaller than that of the control group (FIGS. 1B-E).

Figure 2:
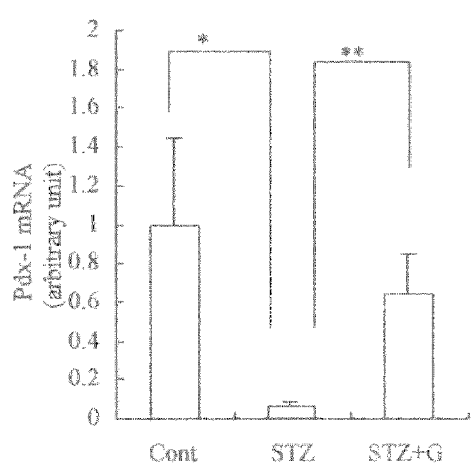
FIG. 2 shows the results for pdx-1 analysis in the pancreas on the 21st day after birth. In this figure, A shows mRNA expression level and B-D show results of immunohistological staining (B shows a control group, C shows an n0-STZ group and D shows an n0-STZ/ghrelin group, respectively with ×500 magnification). In A, "Cont" indicates the control group, "STZ" indicates the n0-STZ group, "STZ+G" indicates the n0-STZ/ghrelin group, and a value for each group is the mean of three observations±SE. In addition, * indicates P<0.0005 and ** indicates P<0.0001.
Figure 2:
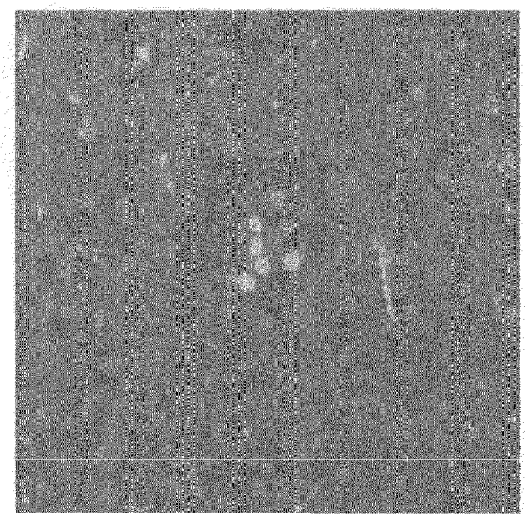
Figure 2:
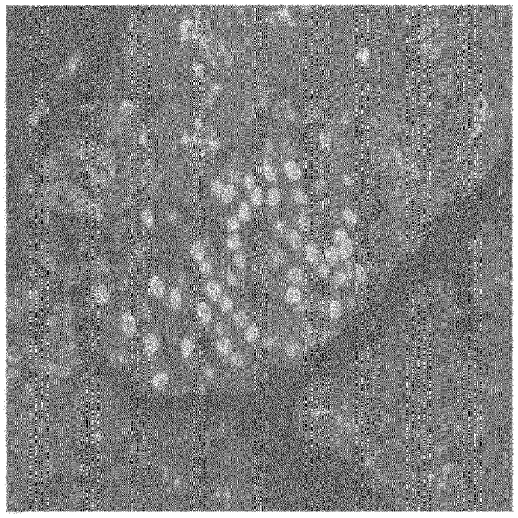
Figure 2:
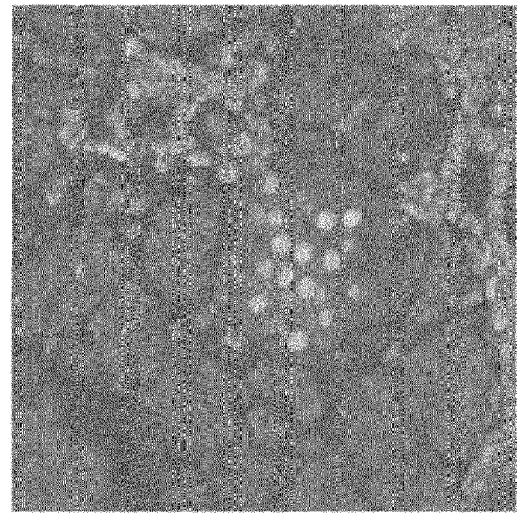

To explore the mechanism governing the alteration of insulin expression in the pancreas, we examined the expression of pdx-1, one of the major transcription factors for differentiation of a pancreas. Pdx-1 mRNA and protein levels changed in a manner similar to those of insulin (FIGS. 2A-D). Though gene expression levels of pdx-1 in the n0-STZ group were less than 1/10 of the level of the control group, the levels of the n0-STZ/ghrelin group following rat ghrelin treatment were recovered to the levels similar to those in the control group (FIG. 2A). Immunofluorescence staining of pdx-1 in a pancreas was in agreement with the results of insulin staining (FIGS. 2B-D).

Thus, this n0-STZ model exhibited diminished insulin production on the 21st day, while blood glucose levels were not altered. Suppression of a decrease in insulin production in this model by the rat ghrelin treatment was confirmed at an mRNA level and a protein level.

Since the n0-STZ model is known to gradually develop hyperglycemia after becoming 8-10 weeks old, a long-term effect of an early ghrelin treatment in this model was examined. Characteristics of the 10-week-old control group, n0-STZ group and n0-STZ/ghrelin group are shown in Table 2.

TABLE 2

|  | Control | n0-STZ | n0-STZ/ghrelin |
|---|---|---|---|
| Body Weight (g) | 317 ± 14 (6) | 285 ± 19 (5)*[1] | 248 ± 40 (13)*[2] |
| FBG (mg/dl) | 103.3 ± 15.6 (6) | 213 ± 12.8 (5)*[3] | 137 ± 28.7 (13)#[1] |
| Plasma Insulin (ng/ml) | 1.05 ± 0.25 (6) | 1.75 ± 0.89 (5) | 0.93 ± 0.49 (8) |
| Pancreas Weight (mg) | 414 ± 81 (6) | 520 ± 95 (5) | 556 ± 83 (13) |
| Pancreas Insulin (μg/Pancreas) | 78.6 ± 19.0 (6) | 39.6 ± 31.6 (5) | 92.6 ± 6.9 (8)#[2] |

Each value represents the mean ± SE (the number of rats)
*[1]$P < 0.05$,
*[2]$P < 0.01$,
*[3]$P < 0.0001$; compared to the control group
[1]$P < 0.0001$,
[2]$P < 0.01$; compared to the n0-STZ group The n0-STZ group demonstrated reduced body weight and hyperglycemia as compared to the control group. Though the plasma insulin concentrations of this group were not decreased, the insulin concentration of each animal appeared to be relatively low for elevated glucose concentration (Table 2, FIG. 3A). In fact, the pancreatic insulin levels were reduced as compared to those of the control group (Table 2).

On the other hand, the FBG levels of the n0-STZ/ghrelin group were significantly lower than those of the n0-STZ group, and were not significantly higher than those of the control group. In addition, the pancreatic insulin contents were maintained at a level as high as those of the control group. Body weights of the n0-STZ/ghrelin group were significantly lower than those of the control group, but were not different from those of the n0-STZ group.

Insulin mRNA expression at the adult stage in the n0-STZ group was still at a low level, though slightly recovered.

Figure 3:
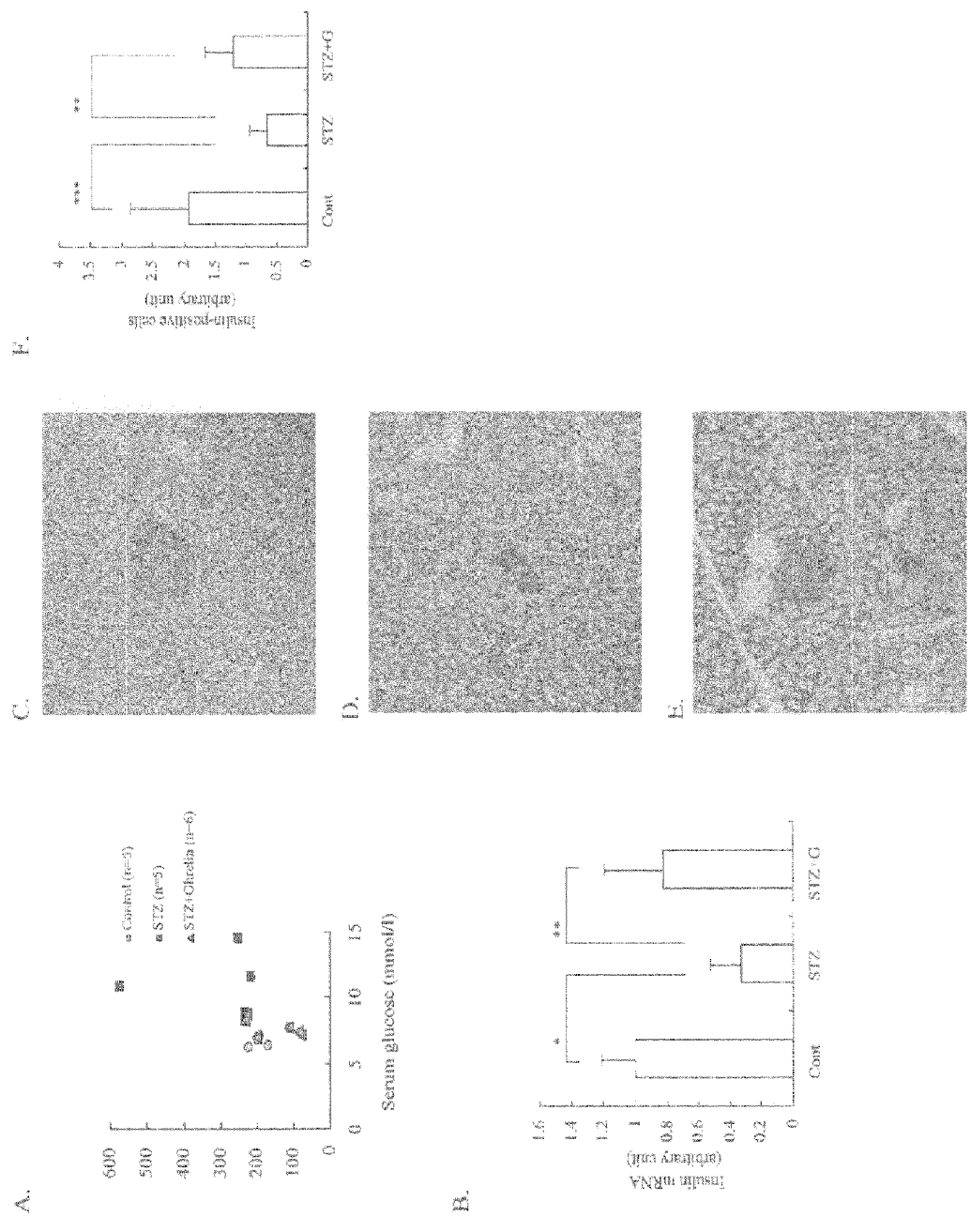
FIG. 3 shows the results for insulin analysis on the 70th day after birth. In this figure, A shows a relationship between blood glucose and insulin concentrations, B is the graph indicating insulin gene expression levels in the pancreas, C-F show results of immunohistological staining of insulin in pancreases (C shows a control group, D shows an n0-STZ group and E shows an n0-STZ/ghrelin group, respectively with ×100 magnification), and F shows a quantification result for an insulin staining-positive cell area. In each of B and F, "Cont" indicates the control group, "STZ" indicates the n0-STZ group, "STZ+G" indicates the n0-STZ/ghrelin group, and the value for each group is the mean of three observations ±SE. In addition, * indicates P<0.001,  indicates P<0.05, and * indicates P<0.01.

The n0-STZ/ghrelin group, on the other hand, showed a level similar to that of the control group as on the 21st day after birth (FIG. 3B). In addition, as for insulin immunohistochemical staining, an islet of Langerhans in the n0-STZ/ghrelin group was larger than that of the n0-STZ group but smaller than that of the control group (FIGS. 3C-F).

Figure 4:
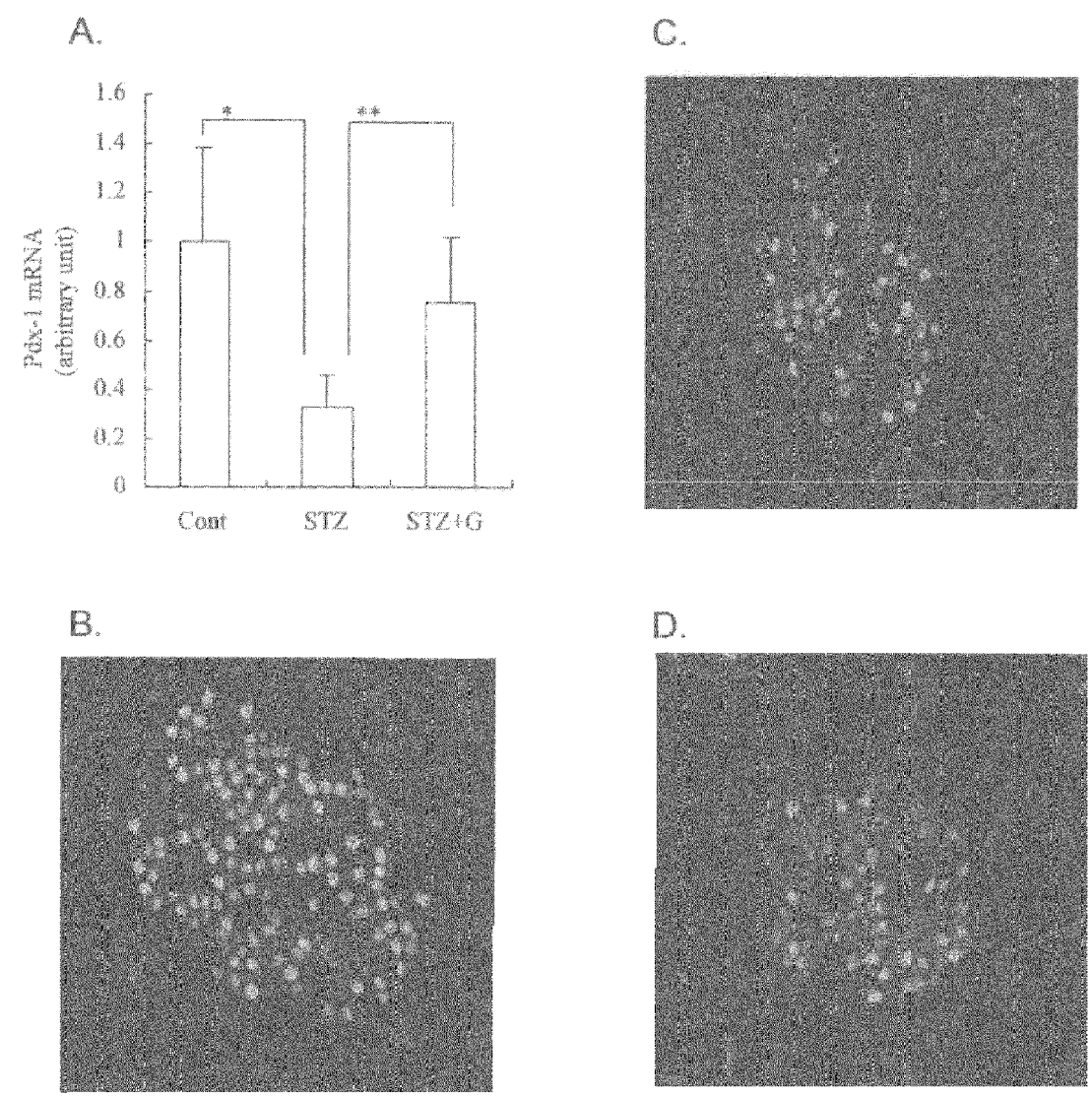
FIG. 4 shows the results for pdx-1 analysis in pancreas on the 70th day after birth. In the drawing, A shows mRNA expression levels and B-D show results of immunohistological staining (B shows a control group, C shows an n0-STZ group and D shows an n0-STZ/ghrelin group, respectively with ×500 magnification). In A, "Cont" indicates the control group, "STZ" indicates the n0-STZ group, "STZ+G" indicates the n0-STZ/ghrelin group, and the value for each group is the mean of three observations±SE. In addition, * indicates P<0.01 and ** indicates P<0.05.

The pattern of mRNA and protein expression levels of pdx-1 in three groups of adult rats was similar to that of the levels on the 21st day after birth (FIG. 4). Pdx-1 gene expression in the n0-STZ group was decreased to approximately ⅓ of that of the control group, while the level in the n0-STZ/ghrelin group was returned to the level close to that of the control group (FIG. 4A). In immunofluorescence staining for pdx-1 in the pancreas, a pattern similar to that of insulin was observed (FIGS. 4B-D).

As described above, in the n0-STZ model, animals developed reduced insulin production in the pancreas and developed hyperglycemia at 10 weeks after birth. Rat ghrelin treatment could inhibit this exacerbation by maintaining or promoting insulin production. Increased expression of pdx-1 may also be partly involved in this maintaining of insulin production. Since increased expression of pdx-1, a transcription factor which plays an important role in development and differentiation of the pancreas, was observed in the n0-STZ/ghrelin group, it is suggested that pancreatic β cells destroyed by STZ administration immediately after birth were regenerated by administration of ghrelin, and regeneration of pancreatic β cells may contribute to maintenance of insulin production.

Example 2

1. Material and Method

Pancreatic sections that had not been used for morphological studies were used to examine β cell replication. The sections were subjected to double staining for phospho-histone H3 (Ser10) and insulin. The sections were incubated overnight with 50-fold dilution of anti-phospho-histone H3 (Ser10) antibody (Cell Signaling Technology) at 4° C. Thereafter, the sections were incubated with guinea pig anti-insulin antibody at a room temperature for 1 hour. After washing with PBS for 6 times, the sections were incubated at a room temperature for 30 minutes in a blocking solution with a secondary antibody conjugated with fluorescence (Alexa Fluor 488 and 546, Molecular Probe). After washing with PBS, sections were mounted with mounting medium containing DAPI (Vector Laboratories) and examined with confocal laser scanning microscopy (Leica Microsystems). At least 1,000β cells were counted per section.

2. Result

Figure 5:
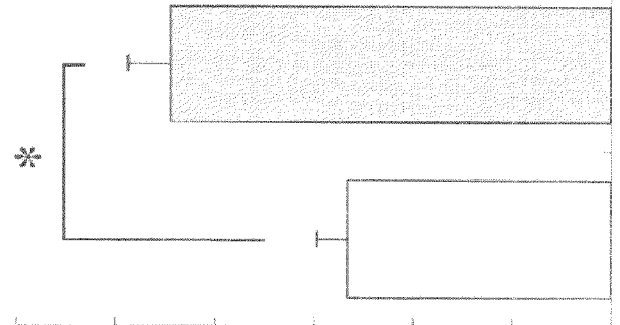
FIG. 5 shows the result of phospho-histone H3 staining to examine replication of β cells in 21-day-old rat. In this figure, A shows a result of immunohistological staining with phospho-histone H3 (green) and insulin (red) for an n0-STZ/ghrelin rat, and B shows phospho-histone H3 labelling index (%) of β cells (out of 1000 cells). "Cont" indicates a control group, "G" indicates ghrelin group, "STZ" indicates an n0-STZ group, "STZ+G" indicates an n0-STZ/ghrelin group, and * indicates P<0.01.
Figure 5:
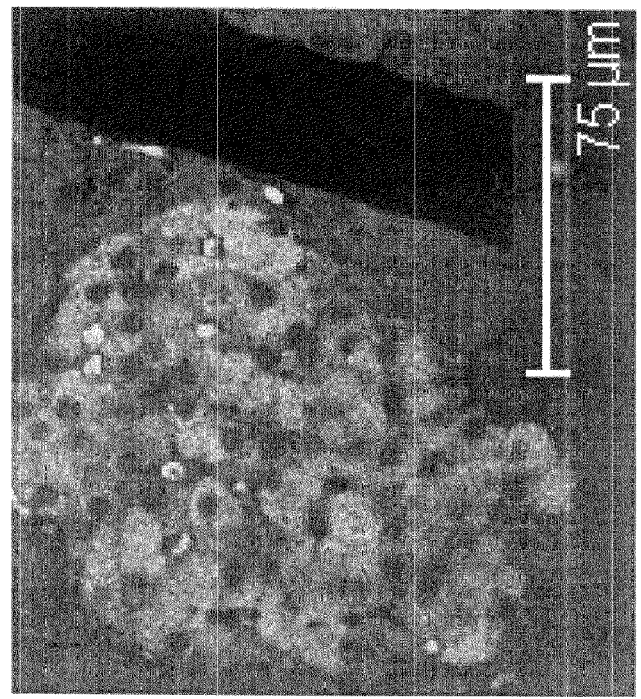
Figure 6:
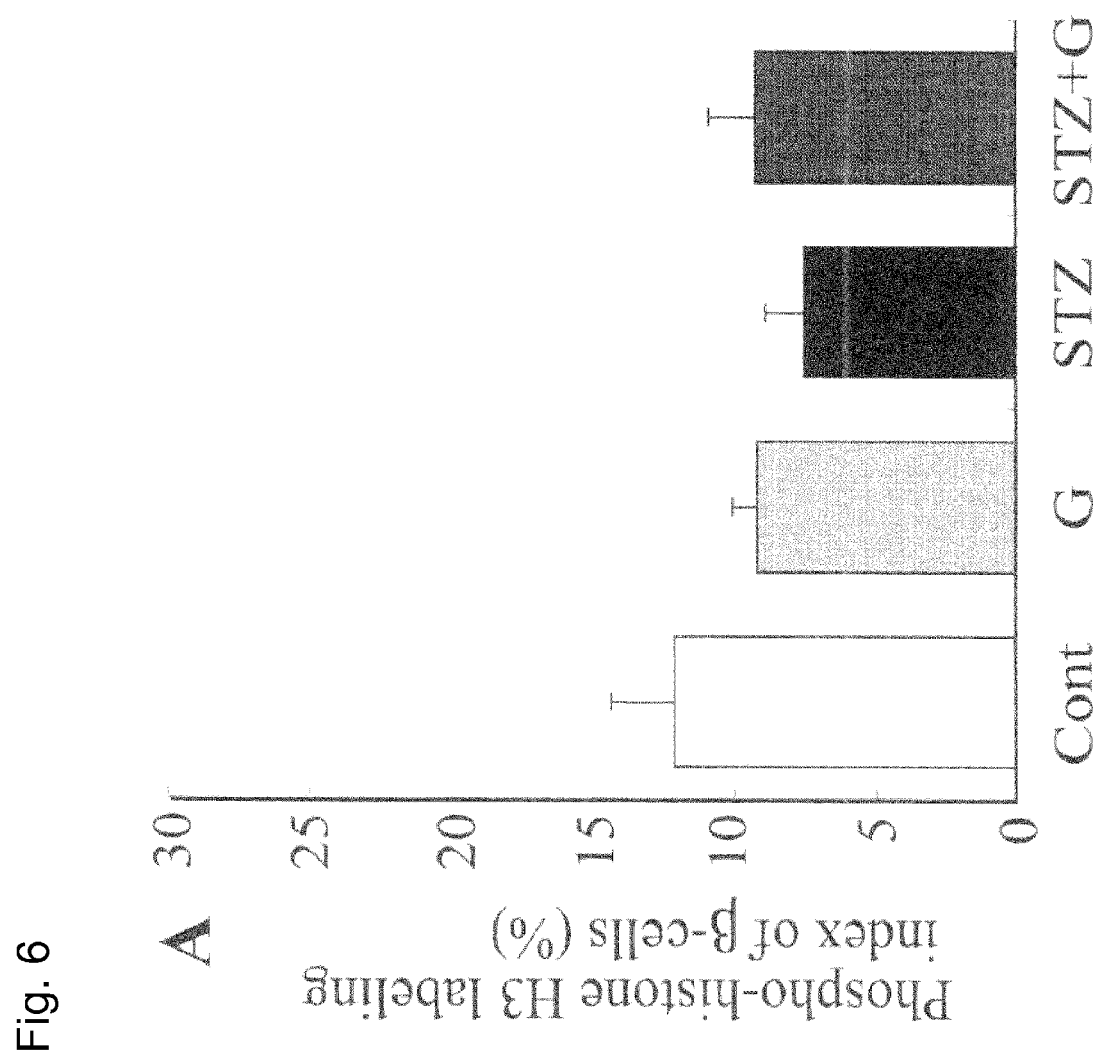
FIG. 6 shows phospho-histone H3 labelling index (%) of β cells in 70-day-old rats. "Cont" indicates a control group, "G" indicates ghrelin group, "STZ" indicates an n0-STZ group, and "STZ+G" indicates an n0-STZ/ghrelin group.

To examine whether β cell proliferation with ghrelin contributed to effects on insulin production and the number of β cells in an STZ-treated rat or not, we performed phospho-histone H3 immunohistochemical analysis. Phospho-histone H3 is a cell proliferation mitosis marker (J. Clin. Invest., 113, pp. 1364-1374, 2004; Br. J. Cancer, 88, pp. 257-262, 2003). The result is shown in FIG. 5A. In 21-day-old rats, double positive cells for phospho-histone H3 and insulin were increased by rat ghrelin treatment approximately 1.7-fold and 15-fold in ghrelin group and the n0-STZ/ghrelin group as compared to control and n0-STZ rats, respectively (FIG. 5B). In 10-week-old rats, though there was no significant difference among four groups, there was a tendency for double positive cells for phospho-histone H3 and insulin to increase by rat ghrelin treatment in STZ model, while the double positive cells were tended to decrease by ghrelin treatment in control group (FIG. 6). Since expressions of pdx-1, insulin and phospho-histone H3 in an n0-STZ/ghrelin rat were significantly increased as compared to levels observed for a 21-day-old control n0-STZ rat, it was suggested that ghrelin stimulated regeneration and replication of β cells in neonatal rats treated with STZ.

Example 3

Since the effect of rat ghrelin was confirmed in the example 1 and the example 2, the effect of human-derived ghrelin (hereafter referred to as human ghrelin, sequence No. 1) was next examined using a neonatal rat STZ model as in the example 1. Human ghrelin is different from rat ghrelin by two amino acids.

1. Material and Method

Sprague Dawley female pregnant rats, purchased from Charles River, were allowed free access to tap water and a standard pellet rat diet (CRF-1, Oriental Yeast Co., Ltd.), and natural deliveries were allowed. Three experimental groups as follows were set: control group wherein rats received single peritoneal injection of citrate buffer immediately after birth; STZ-vehicle group wherein rats received single peritoneal injection of STZ, and then vehicle (5% mannitol solution) was subcutaneously administered twice a day from the 2nd day after birth for 7 days; and STZ-human ghrelin group wherein rats received single peritoneal injection of STZ, and then human ghrelin (sequence No. 1, 100 μg/kg body weight) was subcutaneously injected twice a day from a 2nd day after birth for 7 days.

STZ was prepared and administered as in the example 1. Each male neonatal rat was checked for urinary sugar on the 2nd day with Pretest 3aII (Wako Pure Chemical Industries, Ltd.). Only rats that were glycosuric (3+ value with Pretest 3aII) at day 2 after birth were included in the following studies. The rats were weaned in the evening on the 20th day after birth. Blood samples were collected from tail vein while awake at 8th week (57th day) after birth to measure plasma glucose and insulin concentrations. In addition, after measuring body weight at 9th week (62nd or 63rd day) after birth, blood samples were collected from abdominal aorta under anesthesia with intraperitoneal injection of pentobarbital sodium (50 mg/kg). Whole pancreases were removed and weighed. Thereafter, the pancreases were divided into two pieces and kept for insulin content measurement. Blood samples were centrifuged immediately at 4° C. to prepare plasma samples, and kept at −80° C. until measurement of glucose and insulin concentrations. Glucose concentration was measured using a Glucose CII-test Wako (Wako Pure Chemical Industries, Ltd.), while insulin concentration was measured using a highly sensitive insulin measurement kit (Morinaga Institute of Biological Science, Inc.).

2. Result

Effects of 7 days administration of human ghrelin immediately after STZ administration on plasma glucose and insulin concentrations at 8th week (after 4 hours fasting) were examined. The results are shown in Table 3. Plasma glucose concentrations were significantly increased in the vehicle group as compared to the control group, while glucose concentrations in the STZ-human ghrelin group increased slightly and were not significantly different from those of the control group. Plasma insulin concentrations, on the other hand, were not significantly different among the groups.

TABLE 3

|  | Control | STZ-vehicle | STZ-human ghrelin |
|---|---|---|---|
| Plasma Glucose (mg/dL) | 116.0 ± 1.7 (8) | 330.4 ± 26.5 (9)*[1] | 222.1 ± 10.5 (8) |
| Plasma Insulin (ng/mL) | 2.44 ± 0.12 (8) | 2.07 ± 0.15 (9) | 2.73 ± 0.15 (8) |

Each value is the mean ± SE (the number of rats)
*[1] $P < 0.05$; compared to the control group (Dunnett's multiple comparison test)

Figure 7:
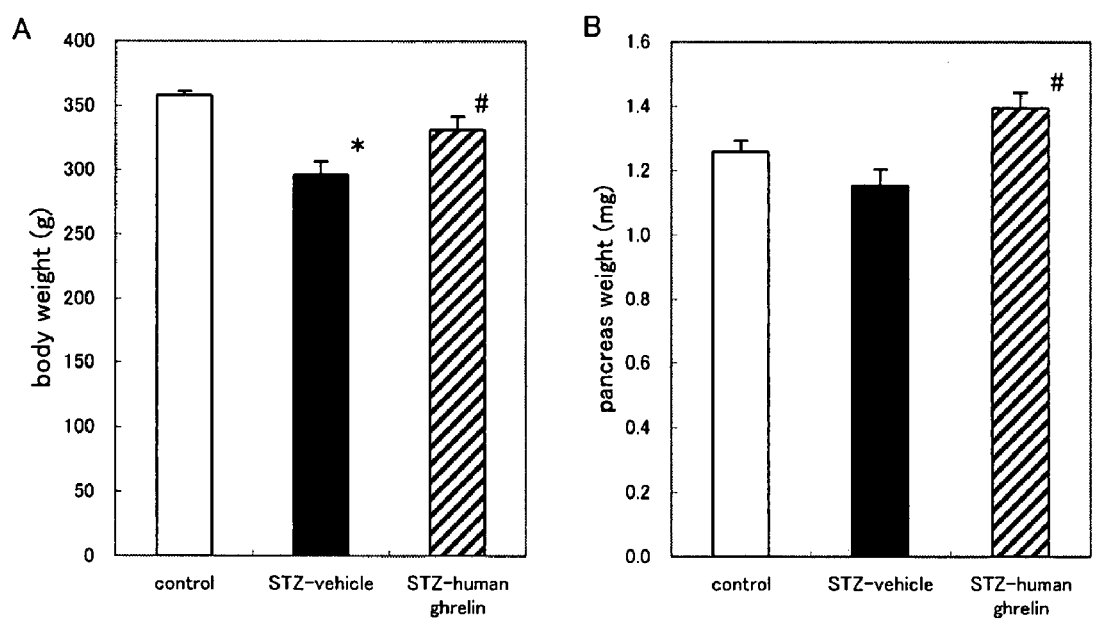
FIG. 7 shows body weights (Panel A) and pancreas weights (Panel B) at 9th week after birth. Control: a normal control group, 8 rats; STZ-vehicle: an STZ-treated vehicle (5% mannitol solution)-administered group, 9 rats; STZ-human ghrelin: an STZ-treated human ghrelin-administered group, 8 rats. Each value is the mean±SE. * indicates P<0.05 compared with a control group, and # indicates P<0.05 compared with an STZ-vehicle group (Dunnett's multiple comparison test).

Then, body weights, pancreas weights, and insulin contents in pancreases at 9th week were analyzed. Results of body weights and pancreas weights are shown in FIG. 7. Though body weights in the STZ-vehicle group were significantly lower than those of the control group, the decrease in body weights in the STZ-human ghrelin group was suppressed and the body weights were comparable to those of the control group. The STZ-vehicle group showed a slightly low value of pancreas weights as compared to the control group. In the STZ-human ghrelin group, on the other hand, pancreas weights were significantly greater than those of the STZ-vehicle group.

Since an increase in the pancreas weights was shown in the STZ-human ghrelin group, insulin contents in pancreases were compared. Pancreases were divided to obtain two samples, spleen-side samples and gut-side samples, and insulin contents in the pancreas was calculated from insulin content of each sample and analyzed. The results are shown in Table 4. In the STZ-vehicle group, the insulin contents in the pancreases calculated from two sites were significantly decreased as compared to the control group. Though insulin contents of the STZ-human ghrelin group were also significantly lower than those of the control group, the contens were about twice as high as those of the STZ-vehicle group.

TABLE 4

|  | Control | STZ-vehicle | STZ-human ghrelin |
|---|---|---|---|
| Insulin Content (Spleen Side) (μg/pancreas) | 454.5 ± 31.6 (8) | 67.1 ± 8.9 (9)*[1] | 120.9 ± 14.1 (8)*[1] |
| Insulin Content (Gut Side) (μg/pancreas) | 309.9 ± 25.8 (7) | 29.4 ± 3.2 (9)*[1] | 63.0 ± 6.7 (8)*[1] |

Each value is the mean value ± SE (the number of rats)
*[1]$P < 0.05$; compared to the control group (Dunnett's multiple comparison test)

From the results above, it was found that human ghrelin treatment immediately after STZ administration in a neonatal STZ model suppresses hyperglycemia and the decrease in body weight in adult state. Since an increase in pancreases weight and a tendency of suppressing a decrease in pancreas insulin contents were also shown, it was suggested that, as are shown in the example 1 for rat ghrelin, pancreatic β cells destroyed by STZ administration immediately after birth were regenerated by administration of human ghrelin and insulin production was partly maintained, which may contributed to suppression of hyperglycemia.

Example 4

Since ghrelin is considered to express its physiological functions via GHS-R, GHS-R agonist compounds other than ghrelin (growth hormone secretagogues, hereafter referred to as GHS compounds) may also promote regeneration of β cells and suppress development of hyperglycemia or diabetes as ghrelin. Therefore, next, a function of a GHS compound was examined using a neonatal STZ model. While various peptide and non-peptide compounds are known as the GHS compounds, a peptide GHS compound GHRP-2 (Ala-D-Trp-Ala-Trp-D-Phe-Lys-NH$_2$, Drugs of the Future 30, pp 124-127, 2005, CAS No. 158861-67-7) was used for examination in this example.

1. Material and Method

Experimental materials, experimental methods and evaluation methods were similar to those in the example 2. As a test substance, 100 μg/kg of GHRP-2 was subcutaneously administered twice a day from a 2nd day after birth for 7 days (an STZ-GHRP-2 group).

2. Result

Effects of early GHRP-2 administration after birth on plasma glucose and insulin concentrations at 8th week (after 4 hours fasting) were examined. The results are shown in Table 6. The plasma glucose concentrations were significantly increased in the STZ-vehicle group as compared to the control group, while in the STZ-GHRP-2 group, the increase was mild and the levels were significantly lower than those of the STZ-vehicle group. Plasma insulin concentrations, on the other hand, were not significantly different among the groups.

TABLE 5

|  | Control | STZ-vehicle | STZ-GHRP-2 |
|---|---|---|---|
| Plasma Glucose (mg/dL) | 116.0 ± 1.7 (8) | 281.6 ± 18.5 (12)*[1] | 145.5 ± 4.1 (12)#[1] |
| Plasma Insulin (ng/mL) | 2.44 ± 0.12 (8) | 2.16 ± 0.10 (12) | 1.89 ± 0.07 (12) |

Each value is the mean ± SE (the number of rats)
*[1]$P < 0.05$; compared to the control group.
[1]$P < 0.05$; compared to the STZ-vehicle group. (Dunnett's multiple comparison test)

Figure 8:
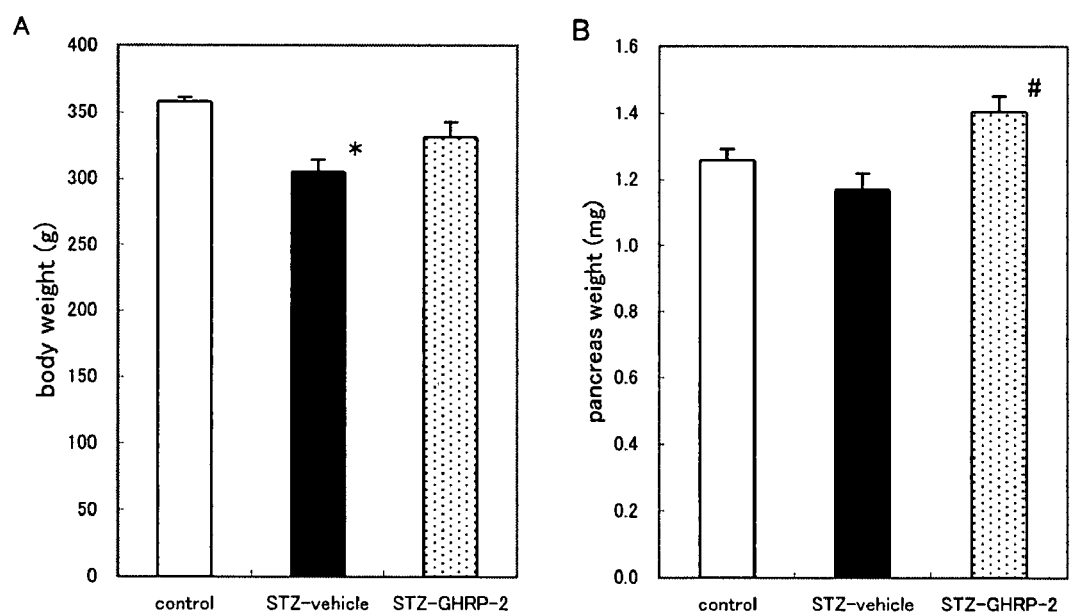
FIG. 8 shows body weights (Panel A) and pancreas weights (Panel B) at 9th week after birth. Control: a normal control group, 8 rats; STZ-vehicle: an STZ-treated vehicle (5% mannitol solution)-administered group, 12 rats; STZ-GHRP-2: an STZ-treated GHRP-2-administered group, 12 rats. Each value is the mean±SE. * indicates P<0.05 compared with a control group (Dunnett's multiple comparison test), and # indicates P<0.05 compared with an STZ-vehicle group (Student's t-test).

Then, body weights, pancreas weights, and insulin contents in pancreases at the 9th week were analyzed. Results of body weights and pancreas weights are shown in FIG. 8. Though body weights in the STZ-vehicle group were significantly lower than those of the control group, the decrease in body weights in the STZ-GHRP-2 group was suppressed and the body weights were not significantly different from those of the control group. The STZ-vehicle group showed a tendency toward decrease in the pancreas weights as compared to the control group. In the STZ-GHRP-2 group, on the other hand, the pancreas weights were greater than those of the STZ-vehicle group.

We compared insulin contents in pancreases. The pancreases were divided to obtain two samples, spleen-side samples and gut-side samples, and the insulin content in the pancreas was calculated from insulin content of each sample, the results are shown in Table 6. In the STZ-vehicle group, the insulin contents in the pancreas in each of two sites were significantly decreased as compared to those of the control group. The insulin contents of the STZ-GHRP-2 group were also significantly lower than those of the control group, but the contents were higher than those of the STZ-vehicle group, which showed a tendency of maintaining insulin production capability.

TABLE 6

|  | Control | STZ-vehicle | STZ-GHRP-2 |
|---|---|---|---|
| Insulin Content (Spleen Side) (μg/pancreas) | 454.5 ± 31.6 (8) | 96.3 ± 7.6 (12)*[1] | 146.8 ± 10.9 (12)*[1] |
| Insulin Content (Gut Side) (μg/pancreas) | 309.9 ± 25.8 (7) | 62.1 ± 5.6 (12)*[1] | 81.7 ± 4.6 (12)*[1] |

Each value is the mean ± SE (the number of cases)
*[1]$P < 0.05$; compared to the control group. (Dunnett's multiple comparison test)

As described above, in addition to rat ghrelin and human ghrelin, GHRP-2 having GHS-R binding and activation capabilities was also shown to have a tendency to improve insulin production capability by early administration to the neonatal STZ model and suppress development of hyperglycemia in adult stage. Therefore, it was suggested that the effects of ghrelin on β cell regeneration and the suppression of hyperglycemia are mediated by GHS-R, and that a compound having GHS-R binding and activation capabilities (GHS) also has similar effects.

As described above, we demonstrated that rat ghrelin, human ghrelin and a GHS compound improved the adult stage hyperglycemia in the neonatal STZ model was shown. Next, the effect of human ghrelin was examined using another hyperglycemia model.

Example 5

A high fat diet of western style is known to be a cause of development of obesity or diabetes. In addition, a fatty acid such as linoleic acid is the ligand of GRP40, one of G protein-coupled receptors, and it has been reported that activation of GPR40 by a fatty acid promotes glucose-responsive insulin secretion from pancreatic β cells (Itoh Y et al. Nature 422, pp 173-176, 2003). On the other hand, it has been suggested that while a short-term load of a fatty acid promotes insulin secretion, a long-term exposure decreases insulin secretion capability and insulin contents in pancreas (Steneberg P et al. Cell Metab 1, pp 245-258, 2005). Therefore, mice were kept with high fatty acid feeds containing linoleic acid to examine the effects of human ghrelin on insulin secretion and blood glucose concentration.

1. Material and Method

Male Crj:CD1(ICR) mice (Charles River Japan) were allowed free access to tap water and a standard pellet mouse diet (CRF-1, Oriental Yeast Co., Ltd.) (with lighting hours from 21 to 9 o'clock). Normal control mice were kept in this condition (normal diet, an ND group). A high fatty acid diet group (High Fat Diet, an HFD group) was allowed to freely take a mixture of 5 g CRF-1 (powder) with 1 g linoleic acid as a high fatty acid diet from the 4th week after birth. As test substances, a vehicle (5% mannitol solution) (an HFD-vehicle group) or 300 µg/kg of human ghrelin (an HFD-ghrelin group) was administered twice a day (once a day in a holiday) for about 7 weeks from the day of the start of high fatty acid diet load. Changes in the body weights and ad lib blood sugar levels after the start of test substance administration were monitored. In addition, mice were fasted overnight on the 50th day from the start of test substance administration, and then linoleic acid (1 mL/kg, intraperitoneal administration) was acutely loaded on a next day to measure plasma glucose and plasma insulin concentrations 1 hour later. The blood sugar value was measured using Antisense II (Horiba, Ltd.), while plasma glucose concentration and insulin concentration were measured using a Glucose CII-test Wako (Wako Pure Chemical Industries, Ltd.) and a Lebis insulin kit (TMB for a mouse) (Shibayagi Co. Ltd.), respectively.

2. Result

Figure 9:
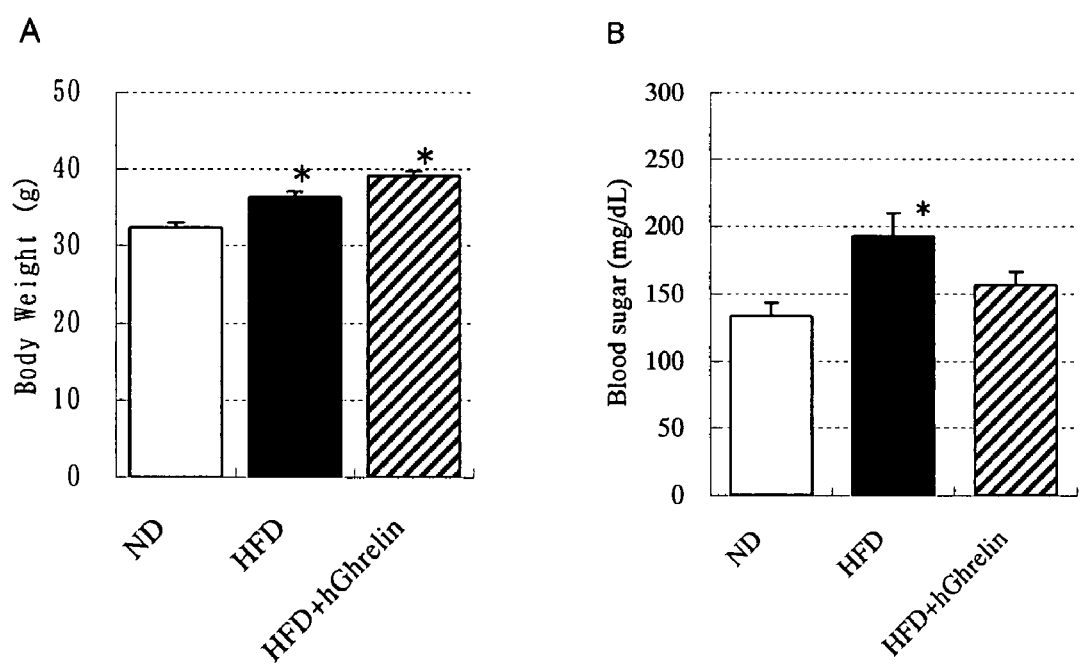
FIG. 9 shows body weights (Panel A) and blood glucose values (Panel B) of mice fed with normal diets or high fatty acid diets. A indicates body weights measured at around 9 a.m. on 42nd day of high fatty acid diet-feeding and test substance administration, and B indicates blood glucose values measured at around 9 a.m. on 43rd day of high fatty acid diet-feeding and test substance administration. ND: a normal diet-fed group; HFD-vehicle: a high fatty acid diet-loaded vehicle (5% mannitol solution)-administered group; HFD-ghrelin: a high fatty acid diet-loaded 300 μg/kg human ghrelin-administered group. The test substance was subcutaneously administered twice in each weekday and once in each holiday. Each value is the mean of 8 mice±standard error. * indicates P<0.05 compared with an ND group (Dunnett's multiple comparison test).

Effects of human ghrelin administration on body weights and blood sugar levels in high fatty acid diet-fed mice were examined. FIG. 9 shows body weights on the 42nd day of administration and ad lib blood sugar levels on the 43rd day of administration. The body weights of mice were higher in the HFD-vehicle group as compared to the ND group, and were further increased in the HFD-ghrelin group. In addition, the blood sugar levels of the HFD-vehicle group were significantly higher than those of the ND group. On the other hand, the blood sugar levels in the HFD-ghrelin group tended to decrease as compared to the HFD-vehicle group, and were not significantly different from those of the ND group. Therefore, ghrelin administration was shown to reduce induction of hyperglycemia by high fatty acid diet.

Next, changes in plasma insulin concentrations and plasma glucose concentrations after acute loading of linoleic acid to high fatty acid diet-loaded mice were analyzed.

Figure 10:
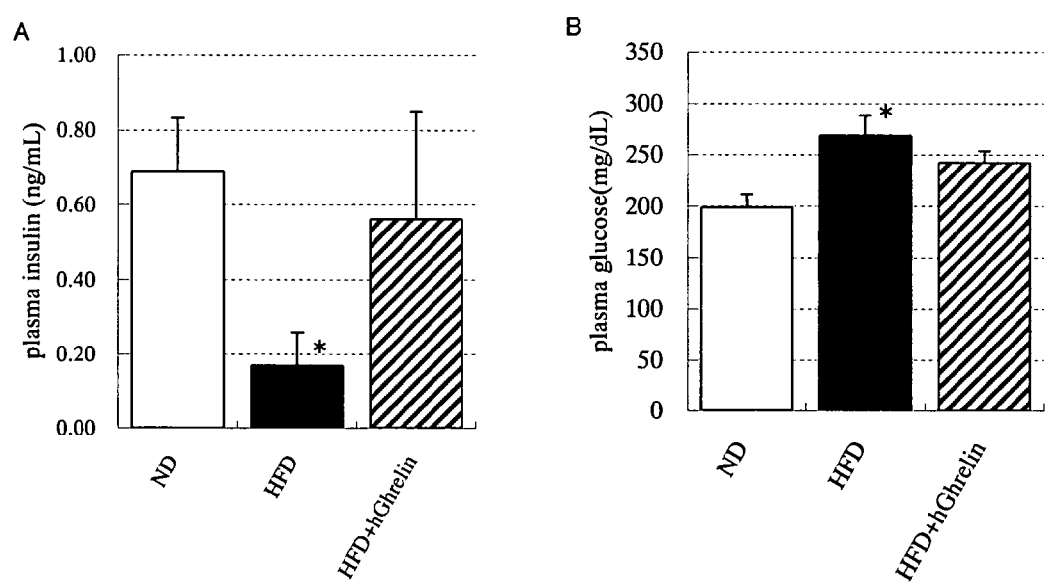
FIG. 10 shows plasma insulin concentrations (Panel A) and plasma glucose concentrations (Panel B) in mice fed with normal diets or high fatty acid diets and subjected to intraperitoneal administration of linoleic acid. After 50 days of high fatty acid diet-feeding and test substance administration, mice were fasted overnight and then subjected to intraperitoneal administration of 1 mL/kg linoleic acid. An hour later, blood was drawn to measure plasma insulin and glucose concentrations. ND: a normal diet-fed group; HFD-vehicle: a high fatty acid diet-loaded vehicle (5% mannitol solution)-administered group; HFD-ghrelin: a high fatty acid diet-loaded 300 μg/kg human ghrelin-administered group. Each value is the mean of 8 mice±SE. * indicates P<0.05 compared with an ND group (Dunnett's multiple comparison test).

FIG. 10 shows plasma insulin concentrations (A) and plasma glucose concentrations (B) in mice fed with normal diets or high fatty acid diets and subjected to intraperitoneal administration of 1 mL/kg of linoleic acid. In the HFD-vehicle group, the plasma insulin concentrations after linoleic acid loading were decreased to at most ⅓ on average as compared to the ND group, suggesting that insulin secretion capability was disturbed by long-term high fatty acid diet loading. The insulin concentrations in the HFD-ghrelin group were higher than those of the HFD-vehicle group, and were not significantly different from those of the ND group (FIG. 10A). On the other hand, though there was almost no difference among 3 groups in plasma glucose concentrations before linoleic acid loading (the ND group: 138±5, the HFD-vehicle group: 146±12, the HFD-ghrelin group: 141±5 mg/dL, the mean of 8 mice±standard error for each group), plasma glucose concentrations were significantly increased in all groups 1 hour after linoleic acid administration as compared to those before administration ($P<0.05$, paired t-test). The increase in the plasma glucose concentrations after linoleic acid administration was more significant in the HFD-vehicle group as compared to the ND group.

The plasma glucose concentrations after linoleic acid loading in the HFD-ghrelin group tended to be low as compared to the HFD-vehicle group, and were not significantly different from those of the ND group (FIG. 10B).

As described above, repeated administration of human ghrelin was shown to suppress an increase in blood sugar levels in high fatty acid diet-loaded mice. With the high fatty acid diet load, the decrease in linoleic acid-induced insulin secretion was observed, which tended to be improved in human ghrelin-administered group. Therefore, it was suggested that human ghrelin improved β cells malfunction, that is, insufficiency of insulin secretion due to high fatty acid diets, and thereby suppressed development of hyperglycemia.

INDUSTRIAL APPLICABILITY

A pharmaceutical of the present invention has a function of promoting neogenesis or regeneration of pancreatic β cells producing and secreting insulin and a function of promoting insulin production in pancreatic β cells, and therefore can suppress or treat hyperglycemia by promoting neogenesis or regeneration of pancreatic β cells producing and secreting insulin in hyperglycemia caused by no insulin secretion or very low insulin secretion due to debility or death of pancreatic β cells, or in hyperglycemia caused by decreased insulin secretion in pancreatic β cells. Furthermore, the pharmaceutical can also be used as a pharmaceutical for regeneration therapy for pancreatic β cells having an insulin-producing function. Since neogenesis or regeneration of pancreatic β cells producing and secreting insulin is enabled according to the present invention, there is an advantage that a fundamental cause of hyperglycemia, that is, deficiency of pancreatic β cells and insufficiency of production or secretion of insulin in the cells can be improved.

The invention claimed is:

1. A method for suppression or treatment of hyperglycemia, which comprises administering an effective amount of a peptide compound or a pharmaceutically acceptable salt thereof, to a patient in need thereof,
wherein the peptide compound is growth hormone-releasing peptide-2 (GHRP-2) or a peptide having an amino acid sequence of any one of SEQ ID NOs: 1 to 21 wherein the 3rd amino acid residue from an amino terminus is a modified amino acid residue wherein a side chain of the amino acid residue is acylated by a fatty acid.

2. The method according to claim 1, wherein hyperglycemia is caused by no insulin secretion or very low insulin secretion due to debility or death of pancreatic β cells, or caused by decreased insulin secretion in pancreatic β cells.

3. The method according to any one of claims 1 and 2, wherein hyperglycemia has a value (ΔIRI/ΔBG) of the difference in values of blood insulin 30 minutes after the load and before the load (ΔIRI) divided by the difference in sugar blood values 30 minutes after the load and before the load (ΔBG) of not more than 0.4.

4. The method according to claim 1, wherein the peptide is selected from the group consisting of (1) a peptide having an amino acid sequence of SEQ ID NO: 1 wherein the 3rd amino acid residue from an amino terminus is a modified amino acid residue having a fatty acid introduced to a side chain of the amino acid residue and (2) GHRP-2.

5. The method according to claim 4, wherein the peptide has an amino acid sequence of SEQ ID NO: 1 and a serine residue in the 3rd position from an amino terminus is a modified amino acid residue having a fatty acid introduced to a hydroxyl group of a side chain of the residue.

6. The method according to claim 5, wherein the peptide has an amino acid sequence of SEQ ID NO: 1 and a hydroxyl group of a side chain of a serine residue in the 3rd position from an amino terminus is acylated by an n-octanoyl group.

7. The method according to claim 4, wherein the peptide is GHRP-2.

8. The method according to claim 1, wherein neogenesis or regeneration of pancreatic β cells is promoted.

9. The method according to claim 1, wherein insulin production in pancreatic β cells is promoted.

10. The method according to claim 1, wherein debility, death or wearing out of pancreatic β cells is suppressed.

11. The method according to claim 1, wherein the peptide compound is GHRP-2 or a peptide having an amino acid sequence of any one of SEQ ID NOs: 1 to 9 and 21 wherein the 3rd amino acid residue from an amino terminus is a modified amino acid residue wherein a side chain of the amino acid residue is acylated by a fatty acid.

* * * * *

SEQUENCE LISTING

<160> NUMBER OF SEQ ID NOS: 27

<210> SEQ ID NO 1
<211> LENGTH: 28
<212> TYPE: PRT
<213> ORGANISM: Homo Sapiens
<220> FEATURE:
<221> NAME/KEY: misc_feature
<223> OTHER INFORMATION: Amino acid sequence for human endogenous
      peptides of growth hormone secretagogue

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 27
<212> TYPE: PRT
<213> ORGANISM: Homo Sapiens
<220> FEATURE:
<221> NAME/KEY: misc_feature
<223> OTHER INFORMATION: Amino acid sequence for human endogenous
      peptides (27 amino acids) of growth hormone secretagogue

<400> SEQUENCE: 2

Gly Ser Ser Phe Leu Ser Pro Glu His Gln Arg Val Gln Arg Lys Glu
1               5                   10                  15

Ser Lys Lys Pro Pro Ala Lys Leu Gln Pro Arg
            20                  25

<210> SEQ ID NO 3
<211> LENGTH: 28
<212> TYPE: PRT
<213> ORGANISM: Rattus norvegicus
<220> FEATURE:
<221> NAME/KEY: misc_feature
<223> OTHER INFORMATION: Amino acid sequence for rat endogenous peptides
      of growth hormone secretagogue

<400> SEQUENCE: 3

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 4
<211> LENGTH: 27
<212> TYPE: PRT
<213> ORGANISM: Rattus norvegicus
<220> FEATURE:
<221> NAME/KEY: misc_feature
<223> OTHER INFORMATION: Amino acid sequence for rat endogenous peptides
      of growth hormone secretagogue

<400> SEQUENCE: 4

Gly Ser Ser Phe Leu Ser Pro Glu His Gln Lys Ala Gln Arg Lys Glu
1               5                   10                  15

Ser Lys Lys Pro Pro Ala Lys Leu Gln Pro Arg
            20                  25

<210> SEQ ID NO 5
<211> LENGTH: 28

```
<212> TYPE: PRT
<213> ORGANISM: Mus musculus
<220> FEATURE:
<221> NAME/KEY: misc_feature
<223> OTHER INFORMATION: Amino acid sequence for mouse endogenous
      peptides of growth hormone secretagogue

<400> SEQUENCE: 5

Gly Ser Ser Phe Leu Ser Pro Glu His Gln Lys Ala Gln Gln Arg Lys
1               5                   10                  15
Glu Ser Lys Lys Pro Pro Ala Lys Leu Gln Pro Arg
            20                  25

<210> SEQ ID NO 6
<211> LENGTH: 28
<212> TYPE: PRT
<213> ORGANISM: Sus scrofa
<220> FEATURE:
<221> NAME/KEY: misc_feature
<223> OTHER INFORMATION: Amino acid sequence for porcine endogenous
      peptides of growth hormone secretagogue

<400> SEQUENCE: 6

Gly Ser Ser Phe Leu Ser Pro Glu His Gln Lys Val Gln Gln Arg Lys
1               5                   10                  15
Glu Ser Lys Lys Pro Ala Ala Lys Leu Lys Pro Arg
            20                  25

<210> SEQ ID NO 7
<211> LENGTH: 27
<212> TYPE: PRT
<213> ORGANISM: Bos taurus
<220> FEATURE:
<221> NAME/KEY: misc_feature
<223> OTHER INFORMATION: Amino acid sequence for bovine endogenous
      peptides (27 amino acids) of growth hormone secretagogue

<400> SEQUENCE: 7

Gly Ser Ser Phe Leu Ser Pro Glu His Gln Lys Leu Gln Arg Lys Glu
1               5                   10                  15
Ala Lys Lys Pro Ser Gly Arg Leu Lys Pro Arg
            20                  25

<210> SEQ ID NO 8
<211> LENGTH: 27
<212> TYPE: PRT
<213> ORGANISM: Ovis aries
<220> FEATURE:
<221> NAME/KEY: misc_feature
<223> OTHER INFORMATION: Amino acid sequence for ovine endogenous
      peptides (27 amino acids) of growth hormone secretagogue

<400> SEQUENCE: 8

Gly Ser Ser Phe Leu Ser Pro Glu His Gln Lys Leu Gln Arg Lys Glu
1               5                   10                  15
Pro Lys Lys Pro Ser Gly Arg Leu Lys Pro Arg
            20                  25

<210> SEQ ID NO 9
<211> LENGTH: 28
<212> TYPE: PRT
<213> ORGANISM: Canis familiaris
<220> FEATURE:
<221> NAME/KEY: misc_feature
<223> OTHER INFORMATION: Amino acid sequence for dog endogenous peptides
      of growth hormone secretagogue
```

-continued

```
<400> SEQUENCE: 9

Gly Ser Ser Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25

<210> SEQ ID NO 10
<211> LENGTH: 21
<212> TYPE: PRT
<213> ORGANISM: Anguilla japonica
<220> FEATURE:
<221> NAME/KEY: misc_feature
<223> OTHER INFORMATION: Amino acid sequence for eel endogenous peptides
      of growth hormone secretagogue.  This peptide is amidated at
      C-terminus.

<400> SEQUENCE: 10

Gly Ser Ser Phe Leu Ser Pro Ser Gln Arg Pro Gln Gly Lys Asp Lys
1               5                   10                  15

Lys Pro Pro Arg Val
            20

<210> SEQ ID NO 11
<211> LENGTH: 23
<212> TYPE: PRT
<213> ORGANISM: Oncorhynchus mykiss
<220> FEATURE:
<221> NAME/KEY: misc_feature
<223> OTHER INFORMATION: Amino acid sequence for rainbow trout
      endogenous peptides (23 amino acids) of growth hormone
      secretagogue.  This peptide is amidated at C-terminus.

<400> SEQUENCE: 11

Gly Ser Ser Phe Leu Ser Pro Ser Gln Lys Pro Gln Val Arg Gln Gly
1               5                   10                  15

Lys Gly Lys Pro Pro Arg Val
            20

<210> SEQ ID NO 12
<211> LENGTH: 20
<212> TYPE: PRT
<213> ORGANISM: Oncorhynchus mykiss
<220> FEATURE:
<221> NAME/KEY: misc_feature
<223> OTHER INFORMATION: Amino acid sequence for rainbow trout
      endogenous peptides (20 amino acids) of growth hormone
      secretagogue.  This peptide is amidated at C-terminus.

<400> SEQUENCE: 12

Gly Ser Ser Phe Leu Ser Pro Ser Gln Lys Pro Gln Gly Lys Gly Lys
1               5                   10                  15

Pro Pro Arg Val
            20

<210> SEQ ID NO 13
<211> LENGTH: 24
<212> TYPE: PRT
<213> ORGANISM: Gallus domesticus
<220> FEATURE:
<221> NAME/KEY: misc_feature
<223> OTHER INFORMATION: Amino acid sequence for chicken endogenous
      peptides of growth hormone secretagogue

<400> SEQUENCE: 13

Gly Ser Ser Phe Leu Ser Pro Thr Tyr Lys Asn Ile Gln Gln Gln Lys
1               5                   10                  15
```

```
Gly Thr Arg Lys Pro Thr Ala Arg
            20

<210> SEQ ID NO 14
<211> LENGTH: 24
<212> TYPE: PRT
<213> ORGANISM: Gallus domesticus
<220> FEATURE:
<221> NAME/KEY: misc_feature
<223> OTHER INFORMATION: Amino acid sequence for chicken endogenous
      peptides of growth hormone secretagogue

<400> SEQUENCE: 14

Gly Ser Ser Phe Leu Ser Pro Thr Tyr Lys Asn Ile Gln Gln Gln Lys
1               5                   10                  15

Asp Thr Arg Lys Pro Thr Ala Arg
            20

<210> SEQ ID NO 15
<211> LENGTH: 26
<212> TYPE: PRT
<213> ORGANISM: Gallus domesticus
<220> FEATURE:
<221> NAME/KEY: misc_feature
<223> OTHER INFORMATION: Amino acid sequence for chicken endogenous
      peptides of growth hormone secretagogue

<400> SEQUENCE: 15

Gly Ser Ser Phe Leu Ser Pro Thr Tyr Lys Asn Ile Gln Gln Gln Lys
1               5                   10                  15

Asp Thr Arg Lys Pro Thr Ala Arg Leu His
            20                  25

<210> SEQ ID NO 16
<211> LENGTH: 27
<212> TYPE: PRT
<213> ORGANISM: Rana catesbeiana
<220> FEATURE:
<221> NAME/KEY: misc_feature
<223> OTHER INFORMATION: Amino acid sequence for frog endogenous
      peptides of growth hormone secretagogue

<400> SEQUENCE: 16

Gly Leu Thr Phe Leu Ser Pro Ala Asp Met Gln Lys Ile Ala Glu Arg
1               5                   10                  15

Gln Ser Gln Asn Lys Leu Arg His Gly Asn Met
            20                  25

<210> SEQ ID NO 17
<211> LENGTH: 28
<212> TYPE: PRT
<213> ORGANISM: Rana catesbeiana
<220> FEATURE:
<221> NAME/KEY: misc_feature
<223> OTHER INFORMATION: Amino acid sequence for frog endogenous
      peptides of growth hormone secretagogue

<400> SEQUENCE: 17

Gly Leu Thr Phe Leu Ser Pro Ala Asp Met Gln Lys Ile Ala Glu Arg
1               5                   10                  15

Gln Ser Gln Asn Lys Leu Arg His Gly Asn Met Asn
            20                  25

<210> SEQ ID NO 18
<211> LENGTH: 20
```

```
<212> TYPE: PRT
<213> ORGANISM: Tilapia nilotica
<220> FEATURE:
<221> NAME/KEY: misc_feature
<223> OTHER INFORMATION: Amino acid sequence for tilapia endogenous
      peptides of growth hormone secretagogue.  This peptide is amidated
      at C-terminus.

<400> SEQUENCE: 18

Gly Ser Ser Phe Leu Ser Pro Ser Gln Lys Pro Gln Asn Lys Val Lys
1               5                   10                  15

Ser Ser Arg Ile
            20

<210> SEQ ID NO 19
<211> LENGTH: 22
<212> TYPE: PRT
<213> ORGANISM: Silurus asotus
<220> FEATURE:
<221> NAME/KEY: misc_feature
<223> OTHER INFORMATION: Amino acid sequence for catfish endogenous
      peptides of growth hormone secretagogue.  This peptide is amidated
      at C-terminus.

<400> SEQUENCE: 19

Gly Ser Ser Phe Leu Ser Pro Thr Gln Lys Pro Gln Asn Arg Gly Asp
1               5                   10                  15

Arg Lys Pro Pro Arg Val
            20

<210> SEQ ID NO 20
<211> LENGTH: 23
<212> TYPE: PRT
<213> ORGANISM: Silurus asotus
<220> FEATURE:
<221> NAME/KEY: misc_feature
<223> OTHER INFORMATION: Amino acid sequence for catfish endogenous
      peptides of growth hormone secretagogue

<400> SEQUENCE: 20

Gly Ser Ser Phe Leu Ser Pro Thr Gln Lys Pro Gln Asn Arg Gly Asp
1               5                   10                  15

Arg Lys Pro Pro Arg Val Gly
            20

<210> SEQ ID NO 21
<211> LENGTH: 28
<212> TYPE: PRT
<213> ORGANISM: Equus caballus
<220> FEATURE:
<221> NAME/KEY: misc_feature
<223> OTHER INFORMATION: Amino acid sequence for equine endogenous
      peptides of growth hormone secretagogue

<400> SEQUENCE: 21

Gly Ser Ser Phe Leu Ser Pro Glu His His Lys Val Gln His Arg Lys
1               5                   10                  15

Glu Ser Lys Lys Pro Pro Ala Lys Leu Lys Pro Arg
            20                  25

<210> SEQ ID NO 22
<211> LENGTH: 21
<212> TYPE: DNA
<213> ORGANISM: Artificial Sequence
<220> FEATURE:
<223> OTHER INFORMATION: Synthetic Construct
```

-continued

```
<400> SEQUENCE: 22
tagaccatca gcaagcaggt c                                              21

<210> SEQ ID NO 23
<211> LENGTH: 19
<212> TYPE: DNA
<213> ORGANISM: Artificial Sequence
<220> FEATURE:
<223> OTHER INFORMATION: Synthetic Construct

<400> SEQUENCE: 23
cacaccaggt acagagcct                                                 19

<210> SEQ ID NO 24
<211> LENGTH: 22
<212> TYPE: DNA
<213> ORGANISM: Artificial Sequence
<220> FEATURE:
<223> OTHER INFORMATION: Synthetic Construct

<400> SEQUENCE: 24
cacttggtgg aagctctcta cc                                             22

<210> SEQ ID NO 25
<211> LENGTH: 23
<212> TYPE: DNA
<213> ORGANISM: Artificial Sequence
<220> FEATURE:
<223> OTHER INFORMATION: Synthetic Construct

<400> SEQUENCE: 25
gacagggtag tggtgggcct agt                                            23

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
aggaggtgca tacgcagcag                                                20

<210> SEQ ID NO 27
<211> LENGTH: 22
<212> TYPE: DNA
<213> ORGANISM: Artificial Sequence
<220> FEATURE:
<223> OTHER INFORMATION: Synthetic Construct

<400> SEQUENCE: 27
gaggccggga gatgtatttg tt                                             22
```